US010913977B2

(12) United States Patent
Makrigiorgos

(10) Patent No.: US 10,913,977 B2
(45) Date of Patent: Feb. 9, 2021

(54) METHODS AND COMPOSITIONS TO ENABLE ENRICHMENT OF MINOR DNA ALLELES BY LIMITING DENATURATION TIME IN PCR OR SIMPLY ENABLE ENRICHMENT OF MINOR DNA ALLELES BY LIMITING THE DENATURATION TIME IN PCR

(71) Applicant: Dana-Farber Cancer Institute, Inc., Boston, MA (US)

(72) Inventor: Gerassimos Makrigiorgos, Chestnut Hill, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 768 days.

(21) Appl. No.: 14/907,188

(22) PCT Filed: Jul. 21, 2014

(86) PCT No.: PCT/US2014/047373
§ 371 (c)(1),
(2) Date: Jan. 22, 2016

(87) PCT Pub. No.: WO2015/013166
PCT Pub. Date: Jan. 29, 2015

(65) Prior Publication Data
US 2016/0186237 A1    Jun. 30, 2016

Related U.S. Application Data

(60) Provisional application No. 61/857,960, filed on Jul. 24, 2013.

(51) Int. Cl.
*C12Q 1/68* (2018.01)
*C12Q 1/686* (2018.01)
*C12Q 1/6858* (2018.01)

(52) U.S. Cl.
CPC ........... *C12Q 1/686* (2013.01); *C12Q 1/6858* (2013.01)

(58) Field of Classification Search
CPC .................................................. C12Q 1/6858
See application file for complete search history.

(56) References Cited

U.S. PATENT DOCUMENTS

| 5,045,450 | A | 9/1991 | Thilly et al. |
| 5,256,775 | A | 10/1993 | Froehler |
| 5,849,497 | A | 12/1998 | Steinman |
| 6,174,680 | B1 | 1/2001 | Makrigiorgos |
| 7,635,566 | B2 | 12/2009 | Brenner |
| 8,455,190 | B2 | 6/2013 | Makrigiorgos |
| 8,623,603 | B2 | 1/2014 | Makrigiorgos |
| 9,133,490 | B2 | 9/2015 | Candau-Cachon |
| 9,957,556 | B2 | 5/2018 | Makrigiorgos |
| 2002/0045227 | A1 | 4/2002 | Wagener |
| 2003/0092021 | A1 | 5/2003 | Thilly |
| 2004/0166519 | A1 | 8/2004 | Cargill et al. |
| 2005/0089894 | A1* | 4/2005 | Ginns ................. C12Q 1/6876 435/6.11 |
| 2007/0154892 | A1 | 7/2007 | Wain-Hobson et al. |
| 2010/0173311 | A1 | 7/2010 | Grow et al. |
| 2010/0203532 | A1* | 8/2010 | Makrigiorgos ...... C12Q 1/6858 435/6.12 |
| 2011/0217714 | A1* | 9/2011 | Makrigiorgos ...... C12Q 1/6848 435/6.12 |
| 2012/0225421 | A1 | 9/2012 | Richardson et al. |
| 2013/0309724 | A1 | 11/2013 | Candau-Cachon |
| 2014/0051087 | A1* | 2/2014 | Makrigiorgos ...... C12Q 1/6853 435/6.12 |
| 2014/0106362 | A1 | 4/2014 | Makrigiorgos |
| 2018/0282798 | A1 | 10/2018 | Makrigiorgos |

FOREIGN PATENT DOCUMENTS

| CN | 1650028 A | 8/2005 | |
| WO | WO 1990/11369 A1 | 10/1990 | |
| WO | WO 1990/13668 A1 | 11/1990 | |
| WO | WO 1991/14003 A2 | 9/1991 | |
| WO | WO 2002/018659 A2 | 3/2002 | |
| WO | WO 2003/072809 A1 | 9/2003 | |
| WO | WO 2007/106534 A2 | 9/2007 | |
| WO | WO 2009/017784 A2 | 2/2009 | |
| WO | WO-2009017784 A2 * | 2/2009 | ........... C12Q 1/6858 |
| WO | WO 2010/065626 A1 | 6/2010 | |
| WO | WO 2011/112534 A1 | 9/2011 | |
| WO | WO 2012/135664 A2 | 10/2012 | |

OTHER PUBLICATIONS

Bunyan et al. Different denaturation rates between methylated and non-methylated genomic DNA can result in allele-specific PCR amplification. Open Journal of Genetics 1:13-14. (Year: 2011).*
Riesewijk et al. Monoallelic expression of human PEG1/MEST is paralleled by parent-specific methylation in fetuses. Genomics 42:236-244. (Year: 1997).*
Walsh et al. Preferential PCR amplification of alleles: mechanisms and solutions. PCR Methods and Applications 1:2410250. (Year: 1992).*
International Search Report and Written Opinion for PCT/US2014/047373 dated Nov. 12, 2014.
International Preliminary Report on Patentability for PCT/US2014/047373 dated Feb. 4, 2016.
[No Author Listed] COLD-PCR: Very High Sensitivity Mutation Detection. Transgenomic. Jul. 1, 2010: 31 pages. Last accessed at <http://www.transgenomic.com/files/literature/48227300.pdf> on Oct. 25, 2014.
Altschul et al., Gapped BLAST and PSI-BLAST: a new generation of protein database search programs. Nucleic Acids Res. Sep. 1, 1997;25(17):3389-402.

(Continued)

Primary Examiner — Teresa E Strzelecka
Assistant Examiner — Olayinka A Oyeyemi
(74) Attorney, Agent, or Firm — Wolf, Greenfield & Sacks, P.C.

(57) ABSTRACT

The present invention is directed to methods, compositions and reaction mixtures for conducting COLD-PCR, by controlling and varying a preferential denaturation time.

9 Claims, 10 Drawing Sheets

(56) References Cited

OTHER PUBLICATIONS

Boisselier et al., COLD PCR HRM: a highly sensitive detection method for IDH1 mutations. Hum Mutat. Dec. 2010;31(12):1360-5. doi: 10.1002/humu.21365. Epub Nov. 9, 2010.
Chou et al., A comparison of high-resolution melting analysis with denaturing high-performance liquid chromatography for mutation scanning: cystic fibrosis transmembrane conductance regulator gene as a model. Am J Clin Pathol. Sep. 2005;124(3):330-8.
Diehl et al., BEAMing: single-molecule PCR on microparticles in water-in-oil emulsions. Nat Methods. Jul. 2006;3(7):551-9.
Diehl et al., Detection and quantification of mutations in the plasma of patients with colorectal tumors. Proc Natl Acad Sci U S A. Nov. 8, 2005;102(45):16368-73. Epub Oct. 28, 2005.
Dressman et al., Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Gundry et al., Amplicon melting analysis with labeled primers: a closed-tube method for differentiating homozygotes and heterozygotes. Clin Chem. Mar. 2003;49(3):396-406.
Henikoff et al., Amino acid substitution matrices from protein blocks. Proc Natl Acad Sci U S A. Nov. 15, 1992;89(22):10915-9.
Janne et al., A rapid and sensitive enzymatic method for epidermal growth factor receptor mutation screening. Clin Cancer Res. Feb. 1, 2006;12(3 Pt 1):751-8.
Karlin et al., Applications and statistics for multiple high-scoring segments in molecular sequences. Proc Natl Acad Sci U S A. Jun. 15, 1993;90(12):5873-7.
Khrapko et al., Constant denaturant capillary electrophoresis (CDCE): a high resolution approach to mutational analysis. Nucleic Acids Res. Feb. 11, 1994;22(3):364-9.
Kimura et al., Mutant DNA in plasma of lung cancer patients: potential for monitoring response to therapy. Ann N Y Acad Sci. Jun. 2004;1022:55-60.
Li et al., BEAMing up for detection and quantification of rare sequence variants. Nat Methods. Feb. 2006;3(2):95-7.
Li et al., Coamplification at lower denaturation temperature-PCR increases mutation-detection selectivity of TaqMan-based real-time PCR. Clin Chem. Apr. 2009;55(4):748-56. doi:10.1373/clinchem. 2008.113381. Epub Feb. 20, 2009.
Li et al., COLD-PCR: a new platform for highly improved mutation detection in cancer and genetic testing. Biochem Soc Trans. Apr. 2009;37(Pt 2):427-32. doi: 10.1042/BST0370427.
Li et al., Replacing PCR with COLD-PCR enriches variant DNA sequences and redefines the sensitivity of genetic testing. Nat Med. May 2008;14(5):579-84. doi: 10.1038/nm1708. Epub Apr. 13, 2008.
Li et al., Two-round coamplification at lower denaturation temperature-PCR (COLD-PCR)-based sanger sequencing identifies a novel spectrum of low-level mutations in lung adenocarcinoma. Hum Mutat. Nov. 2009;30(11):1583-90. doi: 10.1002/humu.21112.
Liew et al., Genotyping of single-nucleotide polymorphisms by high-resolution melting of small amplicons. Clin Chem. Jul. 2004;50(7):1156-64.
Lipsky et al., DNA melting analysis for detection of single nucleotide polymorphisms. Clin Chem. Apr. 2001;47(4):635-44.
Mamon et al., Preferential amplification of apoptotic DNA from plasma: potential for enhancing detection of minor DNA alterations in circulating DNA. Clin Chem. Sep. 2008;54(9):1582-4. doi:10. 1373/clinchem.2008.104612.
Mancini et al., The use of COLD-PCR and high-resolution melting analysis improves the limit of detection of KRAS and BRAF mutations in colorectal cancer. J Mol Diagn. Sep. 2010;12(5):705-11. doi: 10.2353/jmoldx.2010.100018. Epub Jul. 8, 2010.
Milbury et al., COLD-PCR-enhanced high-resolution melting enables rapid and selective identification of low-level unknown mutations. Clin Chem. Dec. 2009;55(12):2130-43. doi: 10.1373/clinchem.2009. 131029. Epub Oct. 8, 2009.
Milbury et al., Ice-COLD-PCR enables rapid amplification and robust enrichment for low-abundance unknown DNA mutations. Nucleic Acids Res. Jan. 2011;39(1):e2. doi: 10.1093/nar/gkq899. Epub Oct. 11, 2010.
Paez et al., EGFR mutations in lung cancer: correlation with clinical response to gefitinib therapy. Science. Jun. 4, 2004;304(5676):1497-500. Epub Apr. 29, 2004.
Pearson et al., Improved tools for biological sequence comparison. Proc Natl Acad Sci U S A. Apr. 1988;85(8):2444-8.
Smith et al., Comparison of biosequences. Adv Appl Math. Dec. 1981;2(4):482-9. doi:10.1016/01968858(81)90046-4.
Thomas et al., High-throughput oncogene mutation profiling in human cancer. Nat Genet. Mar. 2007;39(3):347-51. Epub Feb. 11, 2007. Erratum in: Nat Genet. Apr. 2007;39(4):567. Macconnaill, Laura E [corrected to MacConaill, Laura].
Thomas et al., Sensitive mutation detection in heterogeneous cancer specimens by massively parallel picoliter reactor sequencing. Nat Med. Jul. 2006;12(7):852-5. Epub Jun. 25, 2006. Erratum in: Nat Med. Oct. 2006;12(10):1220.
Wetmur, DNA probes: applications of the principles of nucleic acid hybridization. Crit Rev Biochem Mol Biol. 1991;26(3-4):227-59.
Partial Supplementary European Search Report for EP12764286.6 dated Nov. 17, 2014.
Extended European Search Report for EP12764286.6 dated Mar. 18, 2015.
Extended European Search Report for EP17196718.5 dated May 14, 2018.
International Preliminary Report on Patentability for PCT/EP2008/006476 dated Feb. 9, 2010.
International Search Report and Written Opinion for PCT/US2008/009248 dated Jan. 6, 2009.
International Preliminary Report on Patentability for PCT/US2008/009248 dated Feb. 2, 2010.
International Search Report and Written Opinion for PCT/US2011/027473 dated Jun. 28, 2011.
International Preliminary Report on Patentability for PCT/US2011/027473 dated Sep. 20, 2012.
Invitation to Pay Additional Fees for PCT/US2012/031527 dated Aug. 28, 2012.
International Search Report and Written Opinion for PCT/US2012/031527 dated Nov. 5, 2012.
International Preliminary Report on Patentability for PCT/US2012/031527 dated Oct. 10, 2013.
[No Author Listed] User Guide for the REVEAL Kit KRAS Exon 2. A Mutation Enrichment Assay Powered by ICE COLD-PCR. Transgenomic, Inc 2012.
Candau et al., Very High Sensitivity Detection of K-RAS Exon 2 Mutations Using Fast COLD-PCR. AACR 2010 Poster Presentation.
Castellanos-Rizaldos et al., Temperature-tolerant COLD-PCR reduces temperature stringency and enables robust mutation enrichment. Clin Chem. Jul. 2012;58(7):1130-8. doi: 10.1373/clinchem.2012. 183095. Epub May 15, 2012.
Corless et al., Allele-specific polymerase chain reaction for the imatinib-resistant KIT D816V and D816F mutations in mastocytosis and acute myelogenous leukemia. J Mol Diag Nov. 2006;8(5):604-612.
Dominguez et al., Wild-type blocking polymerase chain reaction for detection of single nucleotide minority mutations from clinical specimens. Oncogene. Oct. 13, 2005;24(45):6830-4. Erratum in: Oncogene. Jan. 26, 2006;25(4):656.
Galbiati et al., Novel use of Full COLD-PCR protocol for noninvasive prenatal diagnosis of genetic diseases. Clin Chem. Jan. 2011;57(1):136-8. doi: 10.1373/clinchem.2010.155671. Epub Oct. 25, 2010.
Jeffreys et al., DNA enrichment by allele-specific hybridization (DEASH): a novel method for haplotyping and for detecting low-frequency base substitutional variants and recombinant DNA molecules. Genome Res. Oct. 2003;13(10):2316-24.
Kwok, Finding a needle in a haystack: detection and quantification of rare mutant alleles are coming of age. Clin Chem. May 2000;46(5):593-4.
Luthra et al., COLD-PCR finds hot application in mutation analysis. Clin Chem. Dec. 2009;55(12):2077-8. doi: 10.1373/clinchem.2009. 136143. Epub Oct. 15, 2009.

(56) References Cited

OTHER PUBLICATIONS

Makrigiorgos, PCR-based detection of minority point mutations. Hum Mutat. May 2004;23(5):406-12.
Milbury et al., PCR-based methods for the enrichment of minority alleles and mutations. Clin Chem. Apr. 2009;55(4):632-40. doi:10.1373/clinchem.2008.113035. Epub Feb. 6, 2009.
Nollau et al., Methods for detection of point mutations: performance and quality assessment. IFCC Scientific Division, Committee on Molecular Biology Techniques. Clin Chem. Jul. 1997;43(7):1114-28.
Pinzani et al., BRAFV600E detection in melanoma is highly improved by COLD-PCR. Clin Chim Acta. May 12, 2011;412(11-12):901-5. doi: 10.1016/j.cca.2011.01.014. Epub Jan. 22, 2011.
Shi et al., Ultra-sensitive detection of BRAF V600E and G469A mutations by ICE COLD-PCR and BLOCKer sequencing. Sep. 2011 Poster.
Shi et al., Use of BLOCker Sequencing (BLocking Oligonucleotide Cycle Sequencing) after Ice COLD-PCR for detection of K-RAS and BRAF mutations. May 2011 Poster.
Walker et al., Strand displacement amplification—an isothermal, in vitro DNA amplification technique. Nucleic Acids Res. Apr. 11, 1992;20(7):1691-6.
Wang et al., Determination of human beta(2)-adrenoceptor haplotypes by denaturation selective amplification and subtractive genotyping. Am J Pharmacogenomics. 2001;1(4):315-22.
Zuo et al., Application of COLD-PCR for improved detection of KRAS mutations in clinical samples. Mod Pathol. Aug. 2009;22(8):1023-31. doi:10.1038/modpathol.2009.59. Epub May 8, 2009.

\* cited by examiner

FIG. 1

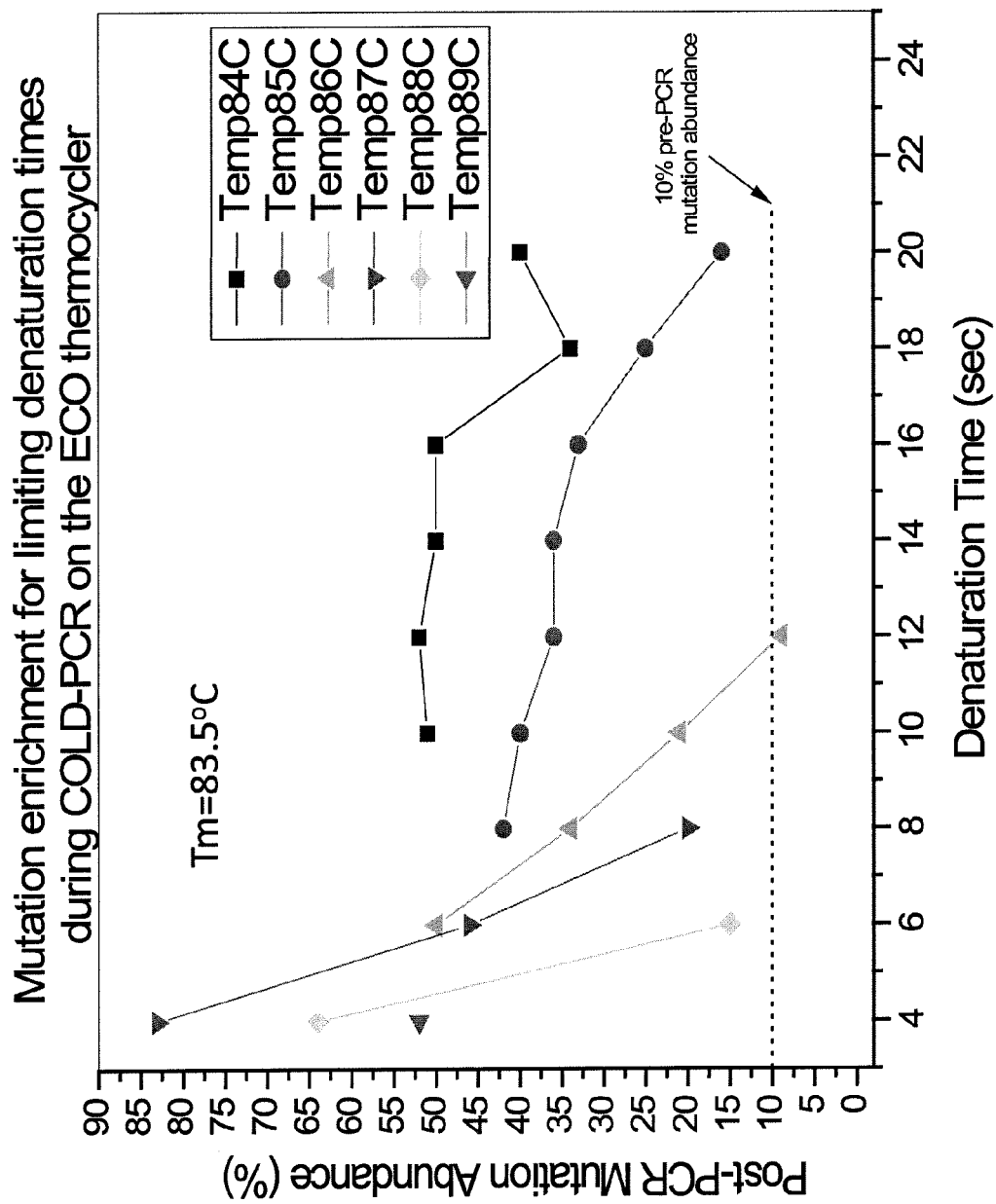

Figure 1: Using the ECO thermocycler, a KRAS DNA fragment with Tm=83.5°C containing 10% initial mutation abundance was amplified using variable denaturation times, and at various temperatures above the Tm. The resulting mutation abundance was derived following Sanger sequencing of the COLD-PCR product. Mutation enrichment is observed over a number of limiting denaturation times and temperatures above the Tm.

Figure 3: Testing limited denaturation time COLD-PCR on a Biorad miniopticon thermocycler: a mutation-specific Taqman probe was used to detect low-level T790M mutations in EGFR exon 20. Limiting the denaturation time increases the discrimination between mutant and wild type samples.

Figure 4: testing limiting denaturation time PCR on a Cepheid thermocycler. A Kras sequence with 10% initial mutation abundance was tested at various temperatures and denaturation times. The relation of the Denaturation time to the Tm of the sequence is noted. The resulting mutation abundance, as detected via Sanger sequencing, is plotted on the Y- axis.

METHODS AND COMPOSITIONS TO ENABLE ENRICHMENT OF MINOR DNA ALLELES BY LIMITING DENATURATION TIME IN PCR OR SIMPLY ENABLE ENRICHMENT OF MINOR DNA ALLELES BY LIMITING THE DENATURATION TIME IN PCR

RELATED APPLICATIONS

This application is a national stage filing under 35 U.S.C. § 371 of International Application No. PCT/US2014/047373, filed Jul. 21, 2014, and entitled "METHODS AND COMPOSITIONS TO ENABLE ENRICHMENT OF MINOR DNA ALLELES BY LIMITING DENATURATION TIME IN PCR OR SIMPLY ENABLE ENRICHMENT OF MINOR DNA ALLELES BY LIMITING THE DENATURATION TIME IN PCR," which claims the benefit under 35 U.S.C. § 119(e) of U.S. Provisional Application No. 61/857,960, filed Jul. 24, 2013, the entire contents of which are hereby incorporated by reference.

BACKGROUND OF THE INVENTION

A commonly encountered situation in genetic analysis entails the need to identify a low percent of variant DNA sequences ('target sequences') in the presence of a large excess of non-variant sequences ('reference sequences'). Examples for such situations include: (a) identification and sequencing of a few mutated alleles in the presence of a large excess of normal alleles; (b) identification of a few methylated alleles in the presence of a large excess of unmethylated alleles (or: vice versa) in epigenetic analysis; (c) identification and genotyping of a few fetal DNA sequences circulating in the blood of the mother where a large excess of mother's DNA sequences are also present; and (d) identification of tumor-circulating DNA in blood of cancer patients (or people suspected of having cancer) in the presence of a large excess of wild-type alleles.

While reliable high throughput screening methods for germline or high-prevalence somatic mutations have recently been described (Thomas, R. K., et al. (2007) Nat Genet, 39, 347-351; Chou, L. S., et al. (2005) Am J Clin Pathol, 124; 330-338; Thomas, R. K., et al. (2006) Nat Med, 12; 852-855) detection of low-prevalence somatic mutations in tumors with heterogeneity, stromal contamination or in bodily fluids is still problematic. And yet, the clinical significance of identifying these mutations is major in several situations. For example: (a) in lung adenocarcinoma, low-level EGFR mutations that cannot be identified by regular sequencing can confer positive response to tyrosine kinase inhibitors (Paez, J. G., et al. (2004) Science, 304; 1497-1500) or drug resistance (Janne, P. A., et al. (2006) Clin Cancer Res, 12; 751-758) (b) mutations in plasma useful as biomarkers for early detection (Diehl, F., et al. (2005) Proc Natl Acad Sci USA, 102; 16368-16373) or tumor response to treatment (Kimura, T., et al. (2004) Ann N Y Acad Sci, 1022; 55-60) cannot be sequenced using conventional methods; and (c) mutations in tumors with frequent stromal contamination, such as pancreatic or prostate, can be 'masked' by presence of wild-type alleles, thus requiring laborious micro-dissection or missing mutations altogether.

A major challenge in molecular diagnosis of human cancer is the remarkable heterogeneity of tumor samples that are to be screened. Human cancer is known to harbor a wide range of chromosomal rearrangements including large deletions, insertions, and translocations, as well as large numbers of somatic mutations. Excluding clonal mutations, most somatic mutations are random and present in only a small fraction of the cancer cells in a tumor. However, these low-level mutations could contribute to tumor progression, and in clinical settings, rapid emergence of resistance to treatment. Contamination of tumor cells with excess normal cells further complicates mutation detection.

The co-occurrence of mutations can complicate matters. An example is provided in reference to lung cancer. Mutations in the ATP binding domain of EGFR predict response to the small tyrosine kinase inhibitor drugs erlotinib and gefitinib. Such mutations, however, do not tell a complete story. Co-occurring mutations in codons 12 and 13 of KRAS predict resistance to anti-EGFR agents, even in the presence of mutations in the ATP binding domain of EGFR. Furthermore, secondary EGFR mutations, especially the mutation T790M (which is present in low frequency), limit the benefit of EGFR targeted therapy due to drug resistance upon prolonged treatment. Similar co-occurring cancer gene mutations have been identified in other cancer types as well. Accordingly, it is desirable to profile individual tumors for potential mutations in several genes simultaneously.

There is, therefore, an increasing demand for rapid and sensitive molecular assays to screen a panel of critical cancer gene mutations for personalized diagnosis and treatment. Of particular interest are certain mutations which sensitize tumors to drug treatment, predict a lack of response or predict emergence of resistance.

To tackle the problems of detecting low level mutations in clinical samples, new forms of PCR (e.g., co-amplification at lower denaturation temperature or COLD-PCR and improved and complete enrichment COLD PCR or ice-COLD-PCR) that amplify preferentially mutation-containing sequences over wild-type alleles have been recently described (Li J, Wang L, Mamon H, Kulke M H, Berbeco R, Makrigiorgos G M. Replacing PCR with COLD-PCR enriches variant DNA sequences and redefines the sensitivity of genetic testing. Nat Med 2008; 14:579-84; Milbury C A, Li J, Makrigiorgos G M. ice COLD-PCR enables rapid amplification and robust enrichment for low-abundance unknown DNA mutations. Nucleic Acids Res; 39:e2). It has been demonstrated that the detection limit of several downstream mutation detection and mutation scanning techniques including sequencing, pyrosequencing, dHPLC, high resolution melting and genotyping can be highly improved via COLD-PCR (Li J, Milbury C A, Li C, Makrigiorgos G M. Two-round coamplification at lower denaturation temperature-PCR (COLD-PCR)-based sanger sequencing identifies a novel spectrum of low-level mutations in lung adenocarcinoma. Hum Mutat 2009; 30:1583-90; Milbury C A, Li J, Makrigiorgos G M. COLD-PCR-enhanced high-resolution melting enables rapid and selective identification of low-level unknown mutations. Clin Chem 2009; 55:2130-43; Mancini I, Santucci C, Sestini R, Simi L, Pratesi N, Cianchi F, et al. The use of COLD-PCR and high-resolution melting analysis improves the limit of detection of KRAS and BRAF mutations in colorectal cancer. J Mol Diagn; 12:705-11; Boisselier B, Marie Y, Labussiere M, Ciccarino P, Desestret V, Wang X, et al. COLD PCR HRM: a highly sensitive detection method for IDH1 mutations. Hum Mutat; 31:1360-5).

COLD-PCR differentiates between mutant and wild type sequences by preferentially amplifying those amplicons that have a lower melting temperature. Thus, the cycling conditions applied during COLD-PCR induce the formation of mutant:wild-type hetero-duplexes during amplification and then denature selectively these hetero-duplexes at a critical denaturation temperature, Tc, that favors denaturation of hetero-duplexes over homoduplexes, (full-COLD-PCR). Successful enrichment during COLD-PCR has been dependent upon the critical denaturation temperature Tc applied for a given amplicon. At the Tc, the target-reference sequence duplexes are substantially denatured, whereas the target-target duplexes and the reference-reference sequence duplexes are substantially undenatured. The value of Tc for a given amplicon is usually just below the value of the melting temperature Tm of the amplicon. To a first approximation, Tc is empirically determined from the melting temperature Tm of an amplicon according to the formula Tc=Tm−1 (Li J, Makrigiorgos G M. COLD-PCR: a new platform for highly improved mutation detection in cancer and genetic testing. Biochem Soc Trans 2009; 37:427-32). For a more precise determination of the optimal Tc, an experimental procedure can be followed to titrate the denaturation temperature over many reactions and determine the optimal Tc. For an additional description of COLD-PCR, see also U.S. Pat. No. 8,455,190, the entire disclosure of which is incorporated herein by reference.

COLD PCR also has been described in connection with multiplexing and with reference blocking sequences. See U.S. Patent publication number 20110217714, the entire disclosure of which is incorporated herein by reference.

SUMMARY OF THE INVENTION

The invention involves a new, unexpected observation that applies to COLD-PCR and all variations of COLD-PCR described in the art (e.g., FAST-COLD-PCR; FULL-COLD-PCR; ICE-COLD-PCR; TEMPERATURE-TOLERANT-COLD-PCR; MULTIPLEX-COLD-PCR; COLD-PCR IN DIGITAL-PCR FORMAT; MODIFIED dNTP COLD-PCR).

In the originally described formats, COLD-PCR discriminates between mutant alleles and wild type alleles by applying denaturation at a critical denaturation temperature (Tc) which is lower than the Tm of the wild type. By applying the (Tc), the duplexes with mismatches will substantially denature whereas the matched wild type duplexes will remain substantially undenatured. The mismatched duplexes containing the mutant strand then can be preferentially amplified.

It has now been discovered that denaturation time can be relied upon to conduct COLD-PCR and to differentiate between mutant and wild-type sequences, even at temperatures at or above the Tm of the wild type duplexes. Specifically, by applying for limited time periods a denaturation temperature at or above the Tm of the wild type, the mutated alleles can be preferentially amplified. COLD-PCR, accordingly, may be carried out more flexibly according to the invention.

One implication of incorporating the 'denaturation time' as a new variable, is making COLD-PCR better adapted to existing PCR machines. There are PCR machines that do not have the ability to regulate the temperature to fractions of a degree (i.e. they can achieve denaturation temperatures at 86 or 87° C. but not at 86.3° C., making it difficult to conduct the COLD-PCR at the optimal Tc. The present observation enables such PCR machines to work well with COLD-PCR, by permitting preferential denaturation of mismatched duplexes at temperature settings existing on the PCR machines, but applying such temperatures for a limited time (a time that results in preferential denaturation for mismatched duplexes). It will be understood that the denaturation time is easy to regulate on all PCR machines.

According to the invention, when a target sequence and reference sequence cross hybridize, minor sequence differences of one or more single nucleotides result in a mismatch(es). A mismatch along a short (e.g., <200 bp) double stranded DNA sequence will generate a small but predictable change in the melting temperature ($T_m$) for that sequence relative to the double stranded reference DNA having no mismatches. (Lipsky, R. H., et al. (2001) Clin. Chem., 47, 635-644; Liew, M., et al. (2004) Clin. Chem., 50, 1156-1164). Depending on the exact sequence context and position of the mismatch, melting temperature changes of 0.5-1.5° C. are common for sequences up to 200 bp. Thus, an annealed target-reference sequence, because of the mismatches, will essentially have a lower $T_m$ than the known allele (i.e., double stranded reference sequence). At least in part, the present disclosure exploits the small $T_m$ difference between fully-matched and mismatched sequences.

As used herein, the term "preferential denaturation time" (tp) is that amount of time, at a given temperature (or range of temperatures) at or above the $T_m$ of a double stranded reference sequence, that will result in the preferential denaturation of double-stranded target sequences that contain mismatches (e.g., mutant:wild-type duplexes) relative to their double stranded reference sequence counterparts (e.g., wild-type duplexes with no mismatches). This permits the selective enrichment of the target sequence containing a mutation during an amplification reaction.

It should be understood that when a reaction mixture containing both double stranded target-reference duplexes (with a mismatch) and double stranded reference duplexes (without a mismatch) is heated to or above the $T_m$ of the double stranded reference duplexes, the target-reference duplexes will begin to melt first. If the heating time is limited (arresting further denaturation), then the target-reference duplexes will have denatured preferentially relative to the double stranded reference duplexes, even though the $T_m$ of the double stranded reference duplexes is reached or exceeded for that limited time. Thus, the preferential denaturation time (tp) may be understood as a window of time during which target-reference duplexes melt prior to, and preferentially to, reference sequence duplexes. The melted target strands (mutation containing strands) then can be amplified preferentially to the unmelted reference strands. Because tp can be applied at every PCR cycle, the differential enrichment of mutation-containing alleles can be compounded exponentially, which results in a large difference in overall amplification efficiency between mutant and wild-type alleles, at the end of the cycling.

Limiting the denaturation time in PCR takes advantage of the increased speed at which mismatch-containing and mutated sequences of lower Tm denature, compared to wild-type sequences and fully-matched sequences. Employing a 'preferential denaturation time, tp' is distinct from differentiating mutant from wild type on the basis of differences in the critical denaturation temperature applied (Tc), which is the way COLD-PCR has been applied thus far.

For example, let it be assumed that a PCR machine is used where the desired denaturation temperature is achieved instantaneously for both mutated and wild type sequences. Let it be assumed that the Tm of the wild type sequences is 84° C. and that the applied denaturation temperature is 85° C. By applying a temperature of 85° C. which is above the Tm, one expects that most sequences will denature. However, by limiting the time over which denaturation is allowed to occur one enables sequences of lower Tm (such as mismatch-containing, mutated sequences in duplex with wild type sequences; or mutated sequences that due to the type of mutation have a lower Tm relative to wild type) to denature first, while wild type sequences with no mismatches remain double stranded, as they need a longer time to denature.

In some embodiments, the tp may be that amount of time necessary to denature between 20% and 80% of the target-reference duplexes, and less than 20%, 15%, 10% and even less than 5% of the double stranded reference duplexes. In some embodiments, the tp may be that amount of time necessary to denature at least 25%, 30%, 40%, 50%, 60%, 70% or even 80% of the target-reference duplexes. In some embodiments, the tp is that amount of time which is less than the amount of time necessary to denature 50%, 40%, 30%, 20%, 10% and even less than 5% of the double stranded reference duplexes.

In some instances, the tp may also preferentially melt a homo-duplex of the mutant (target) sequence. The tp can take advantage of a double stranded target sequence having a lower $T_m$ relative to the double stranded reference duplex.

The tp generally ranges from between about 1 second and 90 seconds, between 1 second and 60 seconds, between 1 second and 45 seconds, between 1 second and 30 seconds, between 1 second and 20 seconds, and even between 1 second and 15 seconds. In some aspects, the tp is 1 second, 2 seconds, 3 seconds, 4 seconds, 5 seconds, 6 seconds, 7 seconds, 8 seconds, 9 seconds, 10 seconds, 11 seconds, 12 seconds, 13 seconds, 14 seconds, 15 seconds, 16 seconds, 17 seconds, 18 seconds, 19 seconds, 20 seconds, 21 seconds, 22 seconds, 23 seconds, 24 seconds, 25 seconds, 26 seconds, 27 seconds, 28 seconds, 29 seconds, or 30 seconds.

The tp is applied at a denaturation temperature (or range of temperatures) that is equal to, or greater than the $T_m$ of the reference sequence. For example, the denaturation temperature set on the PCR machine may be the $T_m$ of the reference sequence (e.g., wild type sequence), or be about 0.1-10° C., 0.1-9° C., 0.1-8° C., 0.1-7° C., 0.1-6° C., 0.2° C.-5° C., 0.3° C.-4.5° C., 0.4-4° C., 0.5-3.5° C., 0.5-3° C., 0.5-3° C., 0.5-2.5° C., 0.5-2° C., 0.5- 1.5° C., 0.5-1° C. above the $T_m$ of the reference sequence. It will be understood that a given temperature setting on a PCR machine will not be reached instantaneously, but instead that temperature will be reached gradually as the machine heats the sample. Therefore, the PCR machine may be set to cool when a particular temperature above the $T_m$ of the reference sequence is reached (whereby the sample has been exposed to a range of temperatures at and above the $T_m$ of the reference sequence, but for a limited period of time) Likewise, the PCR machine may be set to cool when a particular temperature at or above the $T_m$ of the reference sequence has been reached and sustained for a particular limited period of time (whereby the sample has been exposed to a range of temperatures at (and optionally above) the $T_m$ of the reference sequence but again for a limited period of time).

One approach to identify a desirable tp (and denaturation temperature at which tp is applied) in a COLD-PCR reaction, is to run a wild-type sequence in a gradient covering several different denaturation times and temperatures. In parallel, a gradient of mutant sequences and/or heteroduplex mutant/wild-type sequences is run under the same conditions. Once a time (or a window of time) and temperature (or range of temperatures) is identified that enables reproducible generation of robust PCR product for the mutated sequences but not the wild-type sequences, this represents a desirable tp that can be adopted thereafter for the particular region of interest.

According to one aspect of the invention, a method for enriching a target sequence is provided. The method involves:

(a) subjecting a reaction mixture suspected of having a target sequence (that is part of a target sequence duplex) and a reference sequence (that is part of a reference sequence duplex) to a first denaturing temperature that is above the melting temperature (Tm) of the duplexes and for a period of time so as to permit the denaturation of target sequence duplexes and reference sequence duplexes in the reaction mixture, wherein said target sequence is at least 50% homologous to said reference sequence and is amplifiable by the same primer pair as said reference sequence;

(b) reducing the temperature of the reaction mixture so as to permit formation of target strand/reference strand duplexes;

(c) subjecting said reaction mixture to a temperature that is equal to or higher than the Tm of said reference sequence duplex for a time tp causing the preferential denaturation of the target strand/reference strand duplexes of step (b) relative to reference sequence duplexes, to form denatured target strands;

(d) reducing the temperature of the reaction mixture so as to permit said primer pair to anneal to said target strands; and (e) extending said primer pair so as to enrich said target sequence relative to said reference sequence.

In some embodiments, the target sequence is at least 75%, 80%, 85%, 90%, 95% or more than 95% homologous to said reference sequence.

In embodiments, tp is that amount causing at least 10% and not more than 95% denaturation of said target strand/reference strand duplexes. In some embodiments, tp is that amount causing at least 25% and not more than 75% denaturation of said target strand/reference strand duplexes.

In some embodiments, the temperature of step (c) is less than 5° C. higher than the Tm of said reference sequence and tp is between one and ninety seconds. In some embodiments, the temperature of step (c) is less than 2° C. higher than the Tm of said reference sequence. In some embodiments, tp is between one and twenty seconds.

In embodiments, the melting temperature (Tm) and the period of time of step (a) is sufficient to permit the denaturation of at least 95% of said target sequence duplexes and said reference sequence duplexes.

In some embodiments, steps (c)-(e) are repeated one or more times. In some embodiments, steps (a)-(e) are repeated one or more times. In any of the embodiments where steps are repeated, the steps may be repeated 5, 10, 15, 20, 25, 30, 35 40 or more than 40 times, or between 5 and 40 times.

In any of the embodiments, the target and reference sequences may be first amplified by one or more cycles of PCR prior to step (a).

In any of the embodiments, said reference sequence may be a wild-type allele and said target sequence may be a mutant allele.

In any of the embodiments, said target and reference sequences are 15 to 1000 bases, 25 to 500 bases, or 50 to 200 bases.

In any of the embodiments, the method may further involve subjecting said enriched target sequence to further processing. In some embodiments, the further processing can be MALDI-TOF, HR-Melting, Di-deoxy-sequencing, Single-molecule sequencing, pyrosequencing, RFLP, digital PCR or quantitative-PCR.

In any of the embodiments, said target sequence or the reference sequence may be is methylated DNA that has been treated with sodium bisulfite.

In any of the embodiments, the target sequence duplexes may have a lower Tm than said reference sequence duplexes.

In any of the embodiments, the method can further comprise contacting the reaction mixture with reference oligonucleotides. In any of the embodiments, the reference oligonucleotide added can (i) matched the WT-sequence of the anti-sense strand; (ii) be constructed such that PCR primers cannot bind to it; and/or (iii) be phosphorylated on the 3'-end so that it is non-extendable by the polymerase.

In any of the embodiments, the method can be used to enrich two or more different target sequences and the method can further comprise one or more additional pairs of primers specific to said target sequences.

According to another aspect of the invention, a method is provided for enriching a target sequence. The method involves:

(a) subjecting a reaction mixture suspected of having a target sequence (that is part of a target sequence duplex having a first melting temperature (first Tm) and a reference sequence (that is part of a reference sequence duplex having a second melting temperature (second Tm) to a denaturing temperature that is equal to or higher than the second Tm, for a time tp causing the preferential denaturation of the target sequence duplex relative to the reference sequence duplex, wherein said target sequence is at least 50% homologous to said reference sequence;

(b) reducing the temperature of the reaction mixture so as to permit a primer pair to anneal to said target strands; and (c) extending said primer pair so as to enrich said target sequence relative to said reference sequence.

In some embodiments, the target sequence is at least 75%, 80%, 85%, 90%, 95% or more than 95% homologous to said reference sequence. In some embodiments, the reference sequence is amplifiable by said primer pair. In some embodiments, the reference sequence is not amplifiable by said primer pair.

In embodiments, tp is that amount causing at least 10% and not more than 95% denaturation of said target strand/reference strand duplexes. In some embodiments, tp is that amount causing at least 25% and not more than 75% denaturation of said target strand/reference strand duplexes.

In some embodiments, the temperature of step (c) is less than 5° C. higher than the Tm of said reference sequence and tp is between one and ninety seconds. In some embodiments, the temperature of step (c) is less than 2° C. higher than the Tm of said reference sequence. In some embodiments, tp is between one and twenty seconds.

In embodiments, the melting temperature (Tm) and the period of time of step (a) is sufficient to permit the denaturation of at least 95% of said target sequence duplexes and said reference sequence duplexes.

In some embodiments, steps (c)-(e) are repeated one or more times. In some embodiments, steps (a)-(e) are repeated one or more times. In any of the embodiments where steps are repeated, the steps may be repeated 5, 10, 15, 20, 25, 30, 35 40 or more than 40 times.

In any of the embodiments, the target and reference sequences may be first amplified by one or more cycles of PCR prior to step (a).

In any of the embodiments, said reference sequence may be a wild-type allele and said target sequence may be a mutant allele.

In any of the embodiments, said target and reference sequences are 15 to 1000 bases, 25 to 500 bases, or 50 to 200 bases.

In any of the embodiments, the method may further involve subjecting said enriched target sequence to further processing. In some embodiments, the further processing can be MALDI-TOF, HR-Melting, Di-deoxy-sequencing, Single-molecule sequencing, pyrosequencing, RFLP, digital PCR or quantitative-PCR.

In any of the embodiments, said target sequence or the reference sequence may be is methylated DNA that has been treated with sodium bisulfite.

In any of the embodiments, the target sequence duplexes may have a lower Tm than said reference sequence duplexes.

In any of the embodiments, the method can further comprise contacting the reaction mixture with reference oligonucleotides. In any of the embodiments, the reference oligonucleotide added can (i) match the WT-sequence of the anti-sense strand; (ii) be constructed such that PCR primers cannot bind to it; and/or (iii) be phosphorylated or otherwise modified on the 3'-end so that it is non-extendable by the polymerase.

In any of the embodiments, the method can be used to enrich two or more different target sequences and the method can further comprise one or more additional pairs of primers specific to said target sequences.

According to another aspect of the invention, a method is provided for enriching a target sequence. The method involves:

(a) subjecting a reaction mixture suspected of having a target sequence (that is part of a target sequence duplex) and a reference sequence (that is part of a reference sequence duplex) to a first denaturing temperature that is above the melting temperature (Tm) of the duplexes and for a period of time so as to permit the denaturation of target sequence duplexes and reference sequence duplexes in the reaction mixture, wherein said target sequence is at least 50% homologous to said reference sequence;

(b) adding a molar excess of reference oligonucleotides;

(c) reducing the temperature of the reaction mixture so as to permit formation of target strand/reference oligonucleotide duplex and reference sequence/reference oligonucleotide duplex;

(d) subjecting said reaction mixture to a temperature that is equal to or higher than the Tm of said reference sequence/reference oligonucleotide duplex for a time tp causing the preferential denaturation of the target strand/reference strand duplex of step (c) relative to reference sequence/reference oligonucleotide duplex of step (c), to form denatured target strands;

(e) reducing the temperature of the reaction mixture so as to permit a primer pair to anneal to said target strands; and (f) extending said primer pair so as to enrich said target sequence relative to said reference sequence.

In some embodiments, the target sequence is at least 75%, 80%, 85%, 90%, 95% or more than 95% homologous to said reference sequence. In some embodiments, the reference sequence is amplifiable by said primer pair. In some embodiments, the reference sequence is not amplifiable by said primer pair.

In embodiments, tp is that amount causing at least 10% and not more than 95% denaturation of said target strand/reference strand duplexes. In some embodiments, tp is that amount causing at least 25% and not more than 75% denaturation of said target strand/reference strand duplexes.

In some embodiments, the temperature of step (c) is less than 5° C. higher than the Tm of said reference sequence and tp is between one and ninety seconds. In some embodiments, the temperature of step (c) is less than 2° C. higher than the Tm of said reference sequence. In some embodiments, tp is between one and twenty seconds.

In embodiments, the melting temperature (Tm) and the period of time of step (a) is sufficient to permit the denaturation of at least 95% of said target sequence duplexes and said reference sequence duplexes.

In some embodiments, steps (c)-(e) are repeated one or more times. In some embodiments, steps (a) and (c)-(e) are repeated one or more times. In any of the embodiments where steps are repeated, the steps may be repeated 5, 10, 15, 20, 25, 30, 35 40 or more than 40 times.

In any of the embodiments, the target and reference sequences may be first amplified by one or more cycles of conventional PCR prior to step (a).

In any of the embodiments, said reference sequence may be a wild-type allele and said target sequence may be a mutant allele.

In any of the embodiments, said target and reference sequences are 15 to 1000 bases, 25 to 500 bases, or 50 to 200 bases.

In any of the embodiments, the method may further involve subjecting said enriched target sequence to further processing. In some embodiments, the further processing can be MALDI-TOF, HR-Melting, Di-deoxy-sequencing, Single-molecule sequencing, pyrosequencing, RFLP, digital PCR or quantitative-PCR.

In any of the embodiments, said target sequence or the reference sequence may be is methylated DNA that has been treated with sodium bisulfite.

In any of the embodiments, the target sequence duplexes may have a lower Tm than said reference sequence duplexes.

In any of the embodiments, the reference oligonucleotide added in excess can (i) match the WT-sequence of the anti-sense strand; (ii) be constructed such that PCR primers cannot bind to it; and/or (iii) be phosphorylated or otherwise modified on the 3'-end so that it is non-extendable by the polymerase.

In any of the embodiments, the method can be used to enrich two or more different target sequences and the method can further comprise one or more additional pairs of primers specific to said target sequences.

According to another aspect, the present invention is directed to methods for multiplexing to enrich simultaneously several low abundance alleles (mutant target sequences) from a sample. The present invention, in one aspect, relates to multiplex COLD-PCR amplification performed in a space-constrained manner (e.g. in microdroplets, micro-chambers, in pico-litter volumes emulsion, on micro-beads, on glass, or on alternative solid supports; and where one may have just a single DNA molecule as starting material, or just a few molecules of mutant and wild type DNA molecules, as applied for 'digital-PCR'). In some embodiments, a population of DNA fragments having substantially the same melting temperature (iso-Tm DNA amplicons) are simultaneously prepared prior to initiating COLD-PCR/ice-COLD-PCR. The iso-Tm DNA amplicons, in the event there exist both mutant and wild-type sequences present, will typically generate mutant/wild-type heteroduplexes that have substantially the same preferential denaturation time Tp ('isoTp amplicons', i.e. they all denature faster that fully-matched wild-type sequences that are not in heteroduplex formation). In some embodiments, the primers are designed such that a population of DNA amplicons, in the event there exist both mutant and wild-type sequences present, having substantially the same Tm are simultaneously prepared prior to initiating COLD-PCR/ice-COLD-PCR. In some embodiments, COLD-PCR/ice-COLD-PCR amplification is performed on DNA fragments that have different melting temperatures, and therefore different preferential denaturation times tp, in a graded time approach such that mutation enrichment is achieved on all diverse DNA fragments simultaneously (time-independent COLD-PCR, a form of temperature independent or TI-COLD-PCR).

In one aspect of the invention, iso-Tm and/or iso-tp amplicons are prepared from a host's nucleic acids. The iso-Tm and/or iso-tp amplicons, once prepared, can then be used in COLD-PCR or ice-COLD-PCR procedures as described herein, followed by sequencing.

In one embodiment, the COLD-PCR or ice-COLD-PCR procedure is carried out in a space constrained fluid or at a space constrained site on a solid surface. In one embodiment, the procedure is carried out in micro-droplets, each micro-droplet containing only a single pair of primers specific for generating amplicons of a single region of interest. The droplet also contains at least the target sequence to which the pair of primers bind. The droplet may be produced in any number of ways including generating water-in-oil emulsions; or generating oil emulsions in water media. Many droplets can be prepared, different droplets containing different pairs of primers, but all the primers, as described above, generating amplicons that are iso-Tm. COLD-PCR or ice-COLD-PCR then can be performed on hundreds, thousands, or even millions of such droplets simultaneously.

In some embodiments, the method further involves enriching nucleic acids for regions of interest. This can be done in some embodiments prior to carrying out a method of preparing iso-Tm and/or iso-tp amplicons. This can be done in some embodiments after carrying out a method for preparing iso-Tm amplicons. In one embodiment, nucleic acid regions of interest are enriched by contacting the nucleic acids with a plurality of capture oligonucleotides that bind to different regions of interest, permitting binding of the capture oligonucleotides to the regions of interest, and isolating the capture oligonucleotides with the regions of interest bound thereto from remaining nucleic acids. In some embodiments, the capture oligonucleotides are biotinylated at one end. In some embodiments, the capture oligonucleotides are attached to beads. In some embodiments, the capture oligonucleotides are attached as a micro-array to a surface.

In some embodiments, the method further comprises enriching the nucleic acids for regions of interest by contacting the nucleic acids with molecular inversion probes, circularizing the molecular inversion probes such that they encompass the regions of interest, removing non-circularized DNA, and amplifying the regions of interest from the circularized, isolated molecular inversion probes.

According to another aspect of the invention, a method for enriching for target sequences is provided. The method comprises: capturing mutant sequences and wild type sequences within a plurality of droplets, exposing the mutant sequences and wild type sequences within the droplets to a reaction mixture containing pairs of nucleic acid primers, each pair of primers generating under nucleic acid amplification conditions an amplicon that is a copy of a target sequence, wherein the amplicon generated by one pair of primers is different from the amplicon generated from each other pair of primers, wherein the amplicons have substantially the same Tm and wherein each droplet is exposed to only one pair of primers, subjecting the mutant sequences and wild type sequences in the reaction mixture to a first denaturing temperature that is above the melting temperature of the mutant sequences and wild type sequences, reducing the temperature of the reaction mixture to permit the formation of a mutant strand/wild type strand duplexes, subjecting the duplexes in the reaction mixture to a temperature that is equal to or higher than the $T_m$ of said reference sequence duplex for a limited time tp causing the preferential denaturation of the target strand/reference strand duplexes relative to reference sequence duplexes, to form denatured target strands, reducing the temperature of the reaction mixture in the presence of pairs of nucleic acid primers and permitting the primers to anneal to the mutant sequences, and extending the primers to enrich the mutant sequences.

According to another aspect of the invention, a method for enriching for mutant target sequences is provided. The method comprises:

capturing target sequences within a plurality of droplets in such a manner that each droplet contains only copies of a single reference sequence plus only copies of the corresponding target sequence, exposing the target and reference sequences within the droplets to a reaction mixture containing pairs of nucleic acid primers corresponding to the target captured within each droplet and each pair of primers generating under nucleic acid amplification conditions an amplicon that is a copy of a target sequence, wherein the amplicon generated by one pair of primers is different from the amplicon generated from each other pair of primers, wherein the amplicons have substantially the same Tm, and wherein each droplet is exposed to only one pair of primers, only the corresponding region of interest and only the reference sequence corresponding to the region of interest, subjecting the target sequences and the reference sequences in the reaction mixture to a first denaturing temperature that is above the melting temperature of the target sequences and the reference sequences, reducing the temperature of the reaction mixture to permit the formation of a target strand/reference strand duplexes, subjecting the duplexes in the reaction mixture to a temperature that is equal to or higher than the $T_m$ of said reference sequence duplex for a limited time tp causing the preferential denaturation of the target strand/reference strand duplexes relative to reference sequence duplexes, to form denatured target strands, reducing the temperature of the reaction mixture in the presence of pairs of nucleic acid primers and permitting the primers to anneal to the target sequences, and extending the primers to enrich the mutant target sequences.

The reference oligonucleotide is synthetically formed and corresponds to the target sequence. In embodiments, the reference sequence is a copy of at least a portion of the wild-type target sequence. In some embodiments, the reference sequence is the same as the sequence of the target wild-type sequence.

In some embodiments, each pair of primers bind to a host's nucleic acids and generates under nucleic acid amplification conditions an amplicon that is a copy of a region of interest of the host's genome, wherein the amplicon generated by one pair of primers is different from the amplicon generated from each other pair of primers, and wherein the amplicons have substantially the same Tm. In some embodiments, each amplicon is at least 40 nucleotides in length. In some embodiments, the host is a human and each region of interest is known to have or is suspected of having a sequence variation among humans. In some embodiments, the host is a human and at least one region of interest is known to have or is suspected of having a variation at a single nucleotide position within the region of interest. In some embodiments, the host is a bacteria, parasite or virus and each region of interest is known to have or is suspected of having a sequence variation.

In some embodiments, one primer of each pair of primers is attached to a solid substrate, e.g., a bead. In other embodiments, both primers of each pair of primers are attached to a substrate. In some embodiments, the host is a human and the regions of interest comprise a sequence known to be present when there is disease, known to be predictive of disease or known to be predictive of successful treatment of disease with a drug. In some embodiments, one or both primers from each pair of primers have 5'-terminal ends that do not bind the region of interest, wherein the terminal ends of forward primers have the same sequence and the terminal ends of reverse primers have the same sequence. In some embodiments, the at least two pairs of nucleic acid primers is at least 5, 10, 15, 20, 30, 40, 50, 100, 200, 500, 1,000, 5,000, 10,000 or 30,000 pairs of primers. In some embodiments, the kit further comprises a polymerase. In some embodiments, the kit further comprises at least two capture oligonucleotides that bind to different regions of interest. In some embodiments, the kit further comprises beads.

In some embodiments, the at least two different reference oligonucleotides may be provided, each different reference oligonucleotide having a sequence identical to a portion of, or the whole of, a strand of a corresponding amplicon. Each different reference oligonucleotide can exclude the sequence occurring at the ends of the strand of its corresponding amplicon, and each different reference oligonucleotide can be substantially non-overlapping with the pair of primers that generate its corresponding amplicon. In some embodiments, each reference oligonucleotide is biotinylated at one end. In any of the foregoing embodiments, the reference sequence can be a capture sequence.

Finally, it is also known that some genomic regions can be polymorphic (i.e. contain Single Nucleotide Polymorphisms, SNPs, and thus there may be at least two different versions of each region of interest in human genomic DNA). Accordingly, in some embodiment there can be at least two different versions of each reference oligonucleotide, each version representing the different polymorphisms known to exist for a region of interest in genomic DNA, e.g. one version having a G and another having an A for a G/A SNP, and so forth).

According to another aspect of the invention, a method for enriching for mutant target sequences is provided. The method comprises (a) exposing a plurality of target sequences to a reaction mixture containing pairs of nucleic acid primers, each pair of primers generating under nucleic acid amplification conditions an amplicon that is a copy of a target sequence, wherein the amplicon generated by one pair of primers is that of a different target from the amplicon generated from each other pair of primers, (b) subjecting the target sequences in the reaction mixture to a denaturing temperature that is above the melting temperature of wild-type target sequences, (c) reducing the temperature of the reaction mixture to permit the formation of mutant:wild-type target strand heteroduplexes, (d) subjecting the duplexes in the reaction mixture to a temperature that is equal to or higher than the $T_m$ of said reference sequence duplex for a first time tp causing the preferential denaturation of mismatch-containing target strand/reference strand duplexes having a first $T_m$ (e) reducing the temperature of the reaction mixture in the presence of pairs of nucleic acid primers and permitting the primers to anneal to the mutant target sequences,
(f) extending the primers to enrich the mutant target sequences, and
(g) repeating steps (d) to (f) at least once at a second time tp which is longer than the first time tp causing the preferential denaturation of mutant:wild-type target strand heteroduplexes target strand/reference strand duplexes having a second $T_m$ higher than the first $T_m$.

In some embodiments, the reaction mixture comprises a reference sequence that is the same as the wild-type target sequence.

It will be understood that in performing step (g), instead of increasing tp, tp can be held constant and temperature can be further increased incrementally to achieve the same effect. In other words, starting with a temperature at or above the Tm of the reference strands, one can then either further increase temperature while holding tp constant or can increase temperature while holding tp constant to the same effect. As mentioned above, however, it will be more convenient to increase tp incrementally on existing equipment.

In some embodiments, steps (d) to (f) are repeated at least 2, 3, 4, 5, 10, 15, 20, 25, 30, 35, 40, 45, or 50 times at successively increasing critical denaturation temperatures. In some embodiment, at each critical denaturation temperature, steps (d) to (f) are repeated for two or more cycles. In some embodiments, at each critical denaturation temperature, steps (d) to (f) are repeated for 5-40 cycles. In some embodiments, at each critical denaturation temperature, steps (d) to (f) are repeated for 10-30 cycles.

According to another aspect of the invention, a method for enriching for mutant target sequences is provided. The method comprises
(a) exposing the target sequences and reference sequences to a reaction mixture containing pairs of nucleic acid primers, each pair of primers generating under nucleic acid amplification conditions an amplicon that is a copy of a target sequence, wherein the amplicon generated by one pair of primers is that of a different target from the amplicon generated from each other pair of primers,
(b) subjecting the target sequences and the reference sequences in the reaction mixture to a denaturing temperature that is above the melting temperature of the target sequences and the reference sequences,
(c) reducing the temperature of the reaction mixture to permit the formation of a target strand/reference strand duplexes,
(d) subjecting the duplexes in the reaction mixture to a temperature that is equal to or higher than the $T_m$ of said reference sequence duplex for a first time tp causing the preferential denaturation of target strand/reference strand duplexes having a first $T_m$ relative to reference sequence duplexes,
(e) reducing the temperature of the reaction mixture in the presence of pairs of nucleic acid primers and permitting the primers to anneal to the target sequences,
(f) extending the primers to enrich the target sequences,
(g) repeating steps (d) to (f) at least once at a second time tp which is longer than the first time tp causing the preferential denaturation of mutant:wild-type target strand heteroduplexes target strand/reference strand duplexes having a second $T_m$ higher than the first $T_m$.

In some embodiments, the reference sequence is the same as the wild-type target sequence.

As described above, it will be understood that in performing step (g), instead of increasing tp, tp can be held constant and temperature can be further increased incrementally to achieve the same effect. In other words, starting with a temperature at or above the $T_m$ of the reference strands, one can then either further increase temperature while holding tp constant or can increase temperature while holding tp constant to the same effect. As mentioned above, however, it will be more convenient to increase tp incrementally on existing equipment.

In some embodiments, steps (d) to (f) are repeated at least 2, 3, 4, 5, 10, 15, 20, 25, 30, 35, 40, 45, or 50 times at successively increasing critical denaturation temperatures. In some embodiments, at each critical denaturation temperature, steps (d) to (f) are repeated for two or more cycles. In some embodiments, at each critical denaturation temperature, steps (d) to (f) are repeated for 5-40 cycles. In some embodiments, at each critical denaturation temperature, steps (d) to (f) are repeated for 10-30 cycles.

According to another aspect of the invention, a method for enriching for target sequences is provided. The method comprises
(a) exposing the target sequences and reference sequences to a reaction mixture containing pairs of nucleic acid primers, each pair of primers generating under nucleic acid amplification conditions an amplicon that is a copy of a target sequence and a reference sequence, wherein the amplicon generated by one pair of primers is to a different target sequence from the amplicon generated from each other pair of primers,
(b) subjecting the target sequences and the reference sequences in the reaction mixture to a denaturing temperature that is above the melting temperature of the target sequences and the reference sequences,
(c) reducing the temperature of the reaction mixture in the presence of pairs of nucleic acid primers and permitting the primers to anneal to the target sequences,
(d) extending the primers to enrich the target sequences,
(e) subjecting the duplexes in the reaction mixture to a temperature that is equal to or higher than the $T_m$ of said reference sequence duplex for a first time tp causing the preferential denaturation of target strand/reference strand duplexes having a first $T_m$ relative to reference sequence duplexes
(g) repeating steps (c) to (e) at least once at a second time tp which is longer than the first time tp causing the preferential denaturation of mutant/wild-type target strand heteroduplexes target strand/reference strand duplexes having a second $T_m$ higher than the first $T_m$.

As described above, it will be understood that in performing step (g), instead of increasing tp, tp can be held constant and temperature can be further increased incrementally to achieve the same effect. In other words, starting with a temperature at or above the $T_m$ of the reference strands, one can then either further increase temperature while holding tp constant or can increase temperature while holding tp constant to the same effect. As mentioned above, however, it will be more convenient to increase tp incrementally on existing equipment.

In some embodiments, the reference sequence is the same as the wild-type target sequence.

According to another aspect of the invention, a method for preparing a single stranded mutant target sequence from a mixture of target sequences suspected of containing both the mutant target sequence and a wild type target sequence is provided. The method comprises:
(i) subjecting the target sequences to a denaturing temperature that is above the melting temperature of the target sequences, thereby forming a mixture containing the single stranded mutant sequence and single stranded wild type sequences, the mixture characterized by a ratio of single stranded mutant sequences relative to single stranded wild type sequences, (ii) contacting the mixture with an excess of a reference sequence complementary to the wild type sequence, (iii) reducing the temperature to permit formation of target strand/reference strand duplexes, wherein the duplexes include mutant strand/reference strand duplexes and wild type strand/reference strand duplexes, (iv) subjecting the duplexes in the reaction mixture to a temperature that is equal to or higher than the $T_m$ of said reference sequence duplex for a time tp causing the preferential denaturation of the target strand/reference strand duplexes relative to reference sequence duplexes, to form denatured target strands, whereby the ratio of single stranded mutant target sequences relative to single stranded wild type target sequences is increased.

In some embodiments, the method for preparing a single stranded mutant target sequence further comprises (v) reducing the temperature to a critical hybridization temperature (CHT) that permits selective formation of wild-type target sequence/reference sequence duplexes relative to formation of mutant sequence/reference sequence duplexes. In some embodiments, (iv) and (v) are repeated at least 1, 2, 3, 5, 10, 50, 75, 100, 200, 300, 400, 500, 600, 700, 800, 900, or 1000 times to further enrich for the single stranded mutant target sequences.

It will be understood that in performing step (v), instead of reducing the temperature to a CHT, the temperature can be reduced to below the CHT but for a limited period of time, whereby selective formation of wild-type target sequence/reference sequence duplexes relative to formation of mutant sequence/reference sequence duplexes are formed. This can be preferred where the optimal CHT cannot be set on the existing machinery.

In some embodiments, the method for preparing a single stranded mutant target sequence further comprises (vi) after (iv), removing wild type strand/reference strand duplexes, (vii) repeating (iii), (iv) and (vi) at least 1, 2, 3, 5, 10, 50, 75, 100, 200, 300, 400, 500, 600, 700, 800, 900, or 1000 times to further enrich for the single stranded mutant target sequences.

In some embodiments, the method for preparing a single stranded mutant target sequence further comprises (viii) after (iv), removing reference sequences, (ix) adding additional excess of reference sequence, (x) repeating (iii), (iv), (viii) and (ix) at least 1, 2, 3, 5, 10, 50, 75, 100, 200, 300, 400, 500, 600, 700, 800, 900, or 1000 times to further enrich for the single stranded mutant target sequences.

In another aspect of the invention, a method for enriching a target sequence using limited denaturation time is provided, said method comprising:

a. subjecting a reaction mixture suspected of having at least a first target sequence and corresponding first wild type sequence and a second target sequence and corresponding second wild type sequence to a first temperature $T_1$ which is at or above the Tm of said first wild type sequences ($T_{m1}$) but below the Tm of the second wild type sequence ($T_{m2}$) for a limited denaturation time $tp_1$; thereby providing preferential denaturation of the first target sequence containing mutations that reduce the Tm relative to the corresponding 'wild type sequence $T_{m1}$' (e.g. G:C>A:T; or G:C>T:A).

b. reducing the temperature of the reaction mixture so as to allow a primer pair to anneal to denatured target sequence; and c. extending said primer pair so as to enrich said target sequence relative to said wild-type sequence.

d. Repeating a-c for 2-40 cycles to continue amplifying first target sequence over first wild type sequences.

e. Repeating a-d but at a second temperature $T_2$ which is at or above T2 (and is higher than $T_1$) in order to preferentially amplify second target sequence over second wild type sequence that have a melting temperature of $T_{m2}$.

Those skilled in the art that the process can be repeated with a third target sequence and corresponding third wild-type sequence (having a Tm still higher than $T_{m2}$) at a temperature $T_3$, which is higher than $T_2$, and so on until all mutated sequences have been preferentially denatured and amplified. In some embodiments, $T_1$ is just above $T_{m1}$, that is within 0.5, 0.4, 0.3, 0.3 or even 0.1 degrees of $T_{m1}$.

In any of the foregoing embodiments of the method for preparing a single stranded mutant target sequence, the reference sequences may be attached to particles. In any of the foregoing embodiments of the method for preparing a single stranded mutant target sequence, the reference sequences are attached to magnetic particles. In some embodiments, the target sequences in (i) are contacted with an excess of at least two different reference sequences, each different reference sequence being complementary to a different wild-type target sequence, and the duplexes formed by the wild type sequences/reference sequences having substantially the same melting temperature. In some embodiments, the target sequences in (i) are contacted with an excess of at least 10, 15, 20, 30, 40, 50, 100, 200, 500, or 1000 different reference sequences.

In any of the foregoing embodiments of the method for preparing a single stranded mutant target sequence, the method further may comprise detecting the single stranded mutant target sequences. In any of the foregoing embodiments of the method for preparing a single stranded mutant target sequence, the method may further comprise isolating the single stranded mutant target sequences.

In some embodiments, the single stranded mutant target sequences are isolated by: contacting the single stranded mutant target sequences with primers, reducing the temperature to permit binding of the primers to single stranded mutant target sequences, enzymatically extending the primers using biotinylated nucleotides, capturing the biotinylated sequences on a streptavidin-coated solid surface, and removing any unbound sequences, and releasing the single-stranded mutant target sequences from the solid surface.

In some embodiments, the single stranded mutant target sequences are isolated by: adding an excess of biotinylated reference sequences, rapidly reducing the temperature below 50-55° C. to permit formation of single stranded mutant target sequence/biotinylated reference sequence duplexes, treating with exonuclease I to eliminate excess reference sequence, capturing the biotinylated sequences on a streptavidin-coated solid surface, and removing any unbound sequences, and releasing the single-stranded mutant target sequences from the solid surface.

In some embodiments, the single stranded mutant target sequences are isolated by: contacting the formed duplexes with an excess of non-biotinylated adaptor and thermostable ligase at critical hybridization temperature to permit selective ligation of the non-biotinylated adaptor to the duplexes formed by wild-type target sequences with the reference sequences, adding an excess of biotinylated adaptor and thermostable ligase, reducing the temperature to permit formation of mutant target strand/reference strand duplexes, followed by binding of biotinylated adaptor to the formed duplexes, capturing the biotinylated sequences on a streptavidin-coated solid surface, and removing any unbound sequences, and releasing the single-stranded mutant target sequences from the solid surface.

In some embodiments, the single stranded mutant target sequences are isolated by using biotinylated reference sequences, and the duplexes formed by wild type sequence/biotinylated reference sequence are removed by capture on streptavidin-coated solid surface, thereby leaving an enriched population of single-stranded mutant target sequences.

In some embodiments, the single stranded mutant target sequences are isolated by attaching the reference sequences to magnetic beads and the duplexes formed by wild type sequence/reference sequence are removed by removing the magnetic beads.

In any of the foregoing embodiments, the target sequences can be pre-amplified using asymmetric PCR prior to contacting with the reference sequences. In any of the foregoing embodiments, the target sequences can be contacted to the reference sequences in the presence of an organic solvent.

According to another aspect of the invention, a computer readable medium is provided. The medium comprises program instructions for performing any of the methods described herein, above or below.

According to another aspect of the invention, a system for enriching a target sequence is provided. The system includes a memory for implementing the program instructions of any of the computer-readable mediums described herein.

Each of the embodiments and aspects of the invention can be practiced independently or combined. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

These and other aspects of the inventions, as well as various advantages and utilities will be apparent with reference to the Detailed Description. Each aspect of the invention can encompass various embodiments as will be understood.

All documents identified in this application are incorporated in their entirety herein by reference.

BRIEF DESCRIPTION OF THE DRAWINGS

FIG. 1 shows mutation enrichment using LDT-COLD-PCR on an ECO thermocycler. A KRAS DNA fragment with Tm=83.5° C. containing 10% initial mutation abundance was amplified using variable denaturation times, and at various temperatures above the Tm. The resulting mutation abundance was derived following Sanger sequencing of the LDT-COLD-PCR product. Mutation enrichment is observed over a number of limiting denaturation times and temperatures above the Tm.

DETAILED DESCRIPTION OF THE INVENTION

Figure 2A:
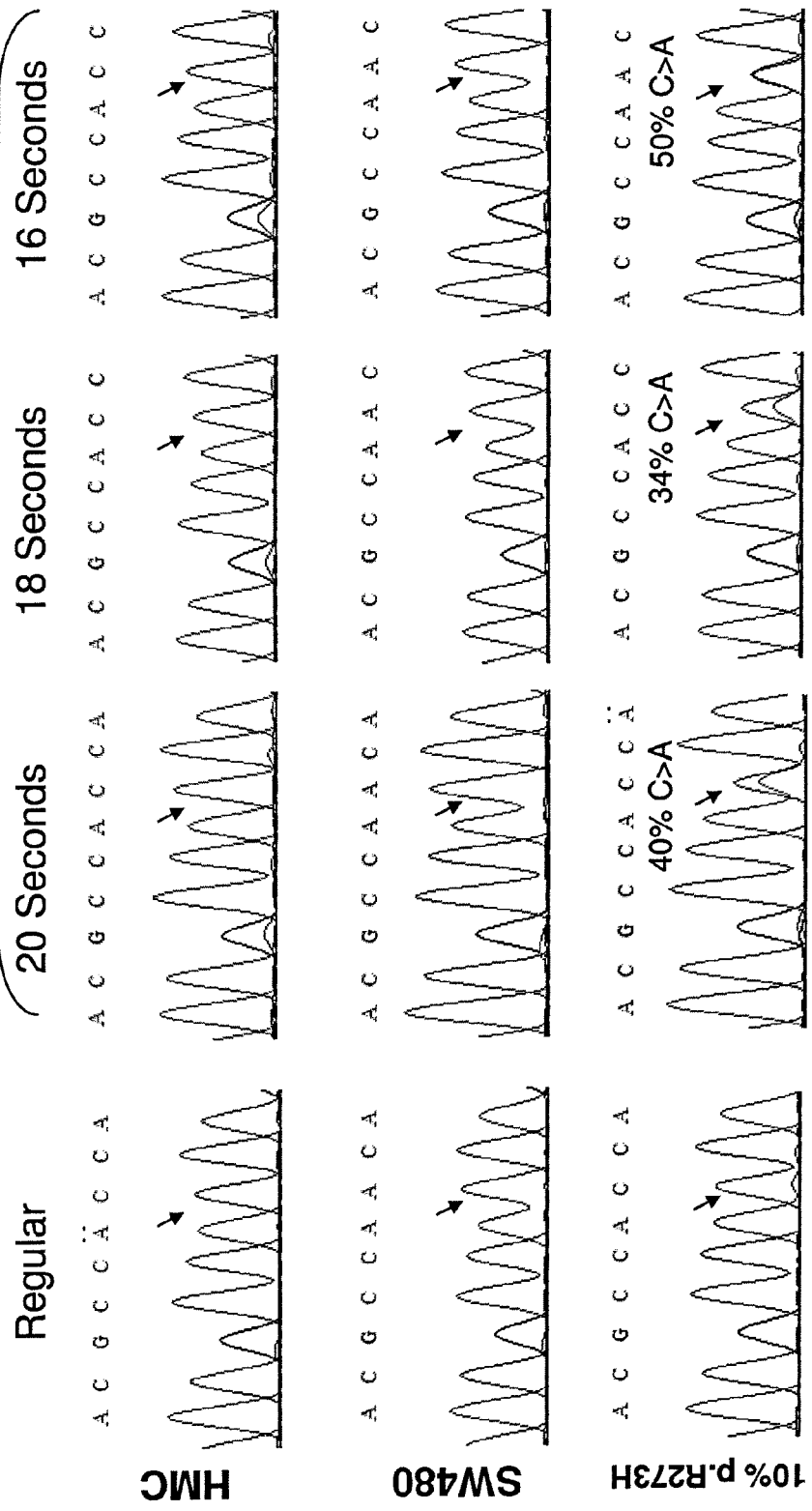
FIG. 2A shows representative chromatograms that depict the results of Sanger sequencing of LDT-COLD-PCR products obtained in the experiment of FIG. 1. The percent enrichment of the mutant sequence, as derived from the chromatogram, is indicated.
Figure 2B:
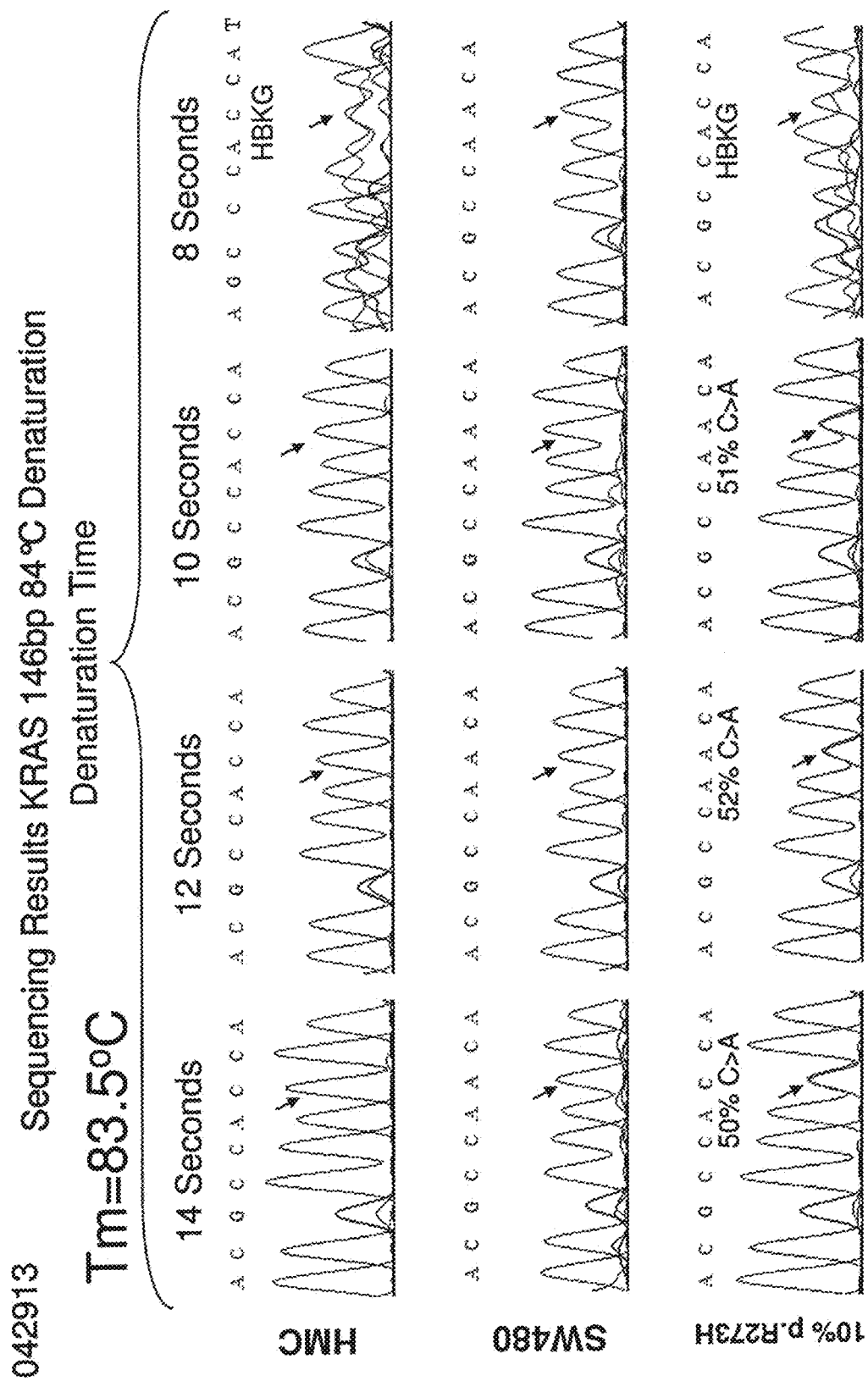
FIG. 2B shows the chromatograms of the LDT-COLD-PCR experiments performed using a denaturation temperature of 84° C. across the indicated limited denaturation times.
Figure 2C:
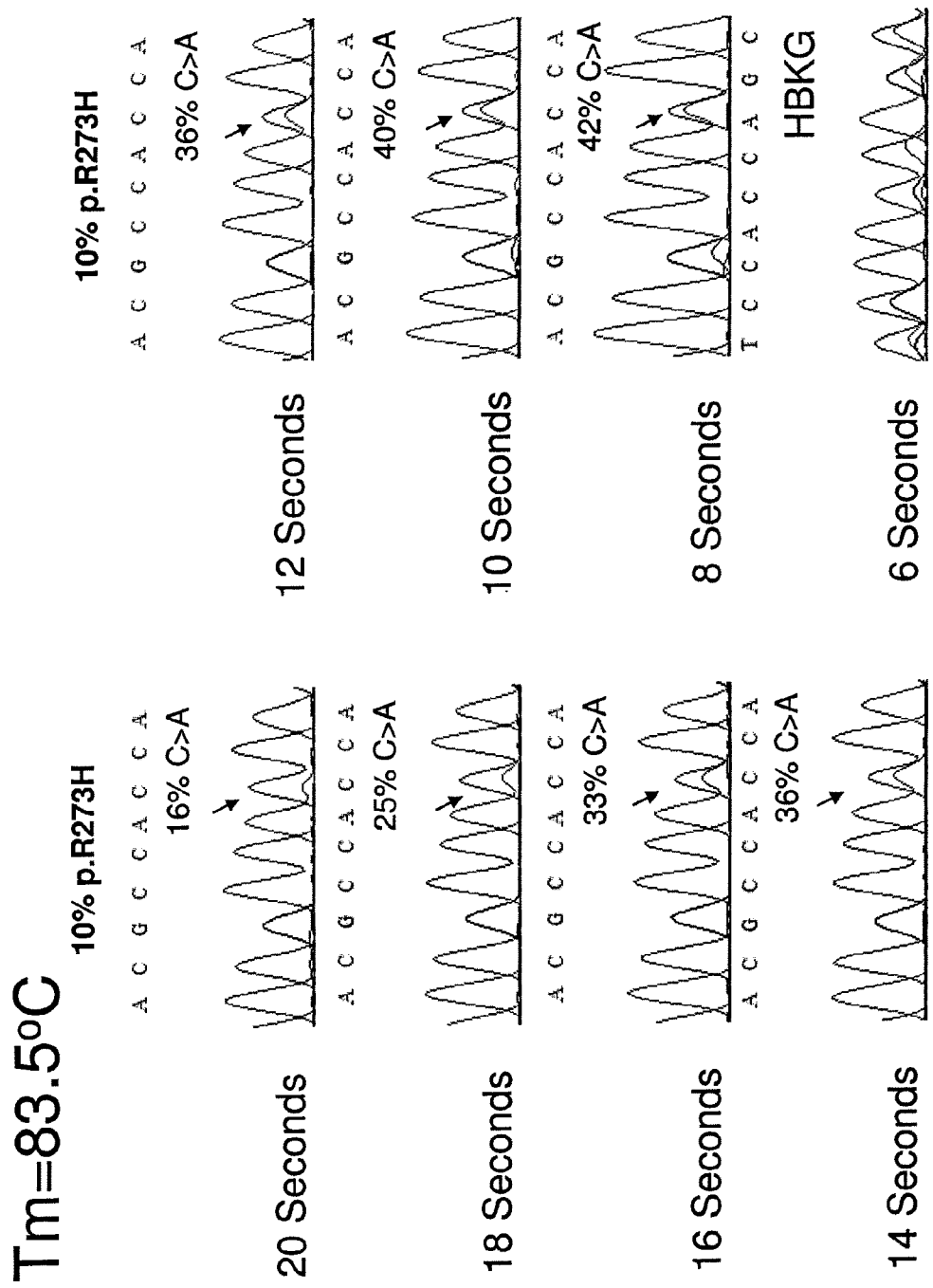
FIG. 2C shows the chromatograms of the LDT-COLD-PCR experiments performed using a denaturation temperature of 85° C. across the indicated limited denaturation times.
Figure 2D:
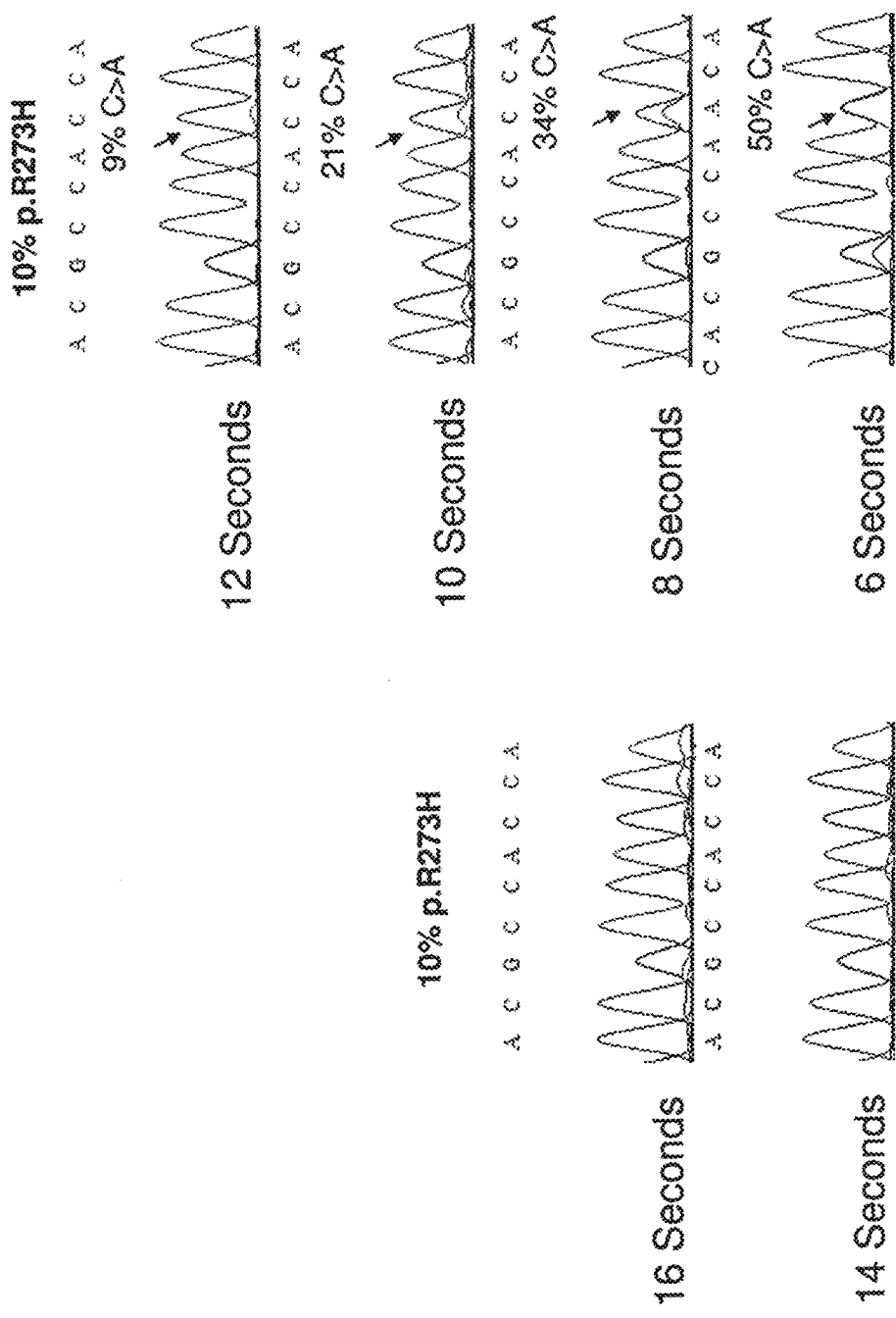
FIG. 2D shows the chromatograms of the LDT-COLD-PCR experiments performed using a denaturation temperature of 86° C. across the indicated limited denaturation times.
Figure 2E:
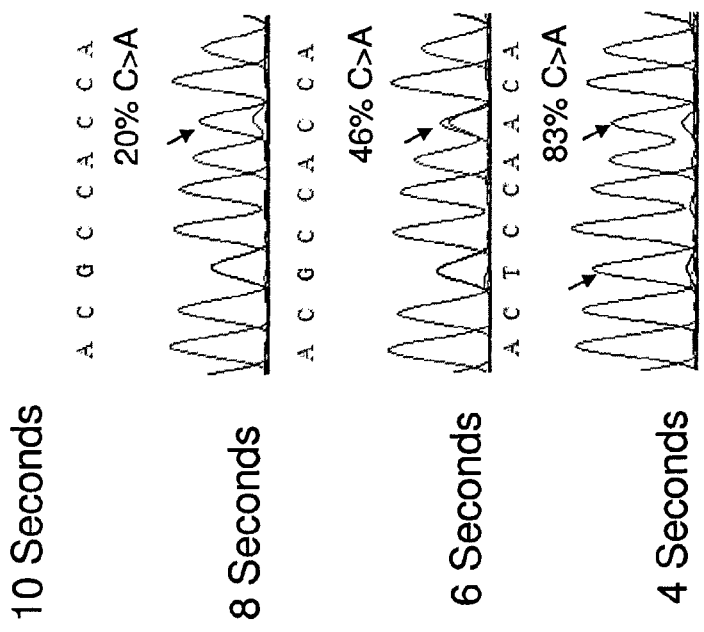
FIG. 2E shows the chromatograms of the LDT-COLD-PCR experiments performed using a denaturation temperature of 87° C. across the indicated limited denaturation times.
Figure 2F:
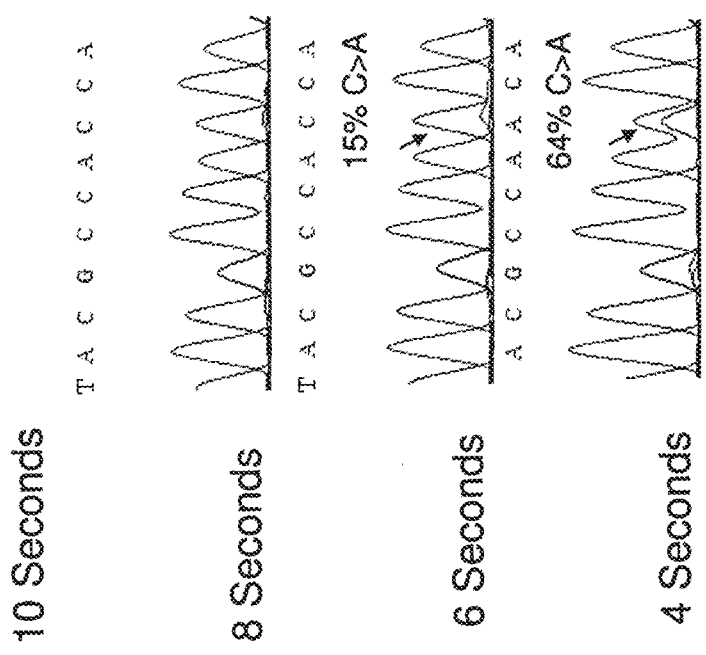
FIG. 2F shows the chromatograms of the LDT-COLD-PCR experiments performed using a denaturation temperature of 88° C. across the indicated limited denaturation times.
Figure 2G:
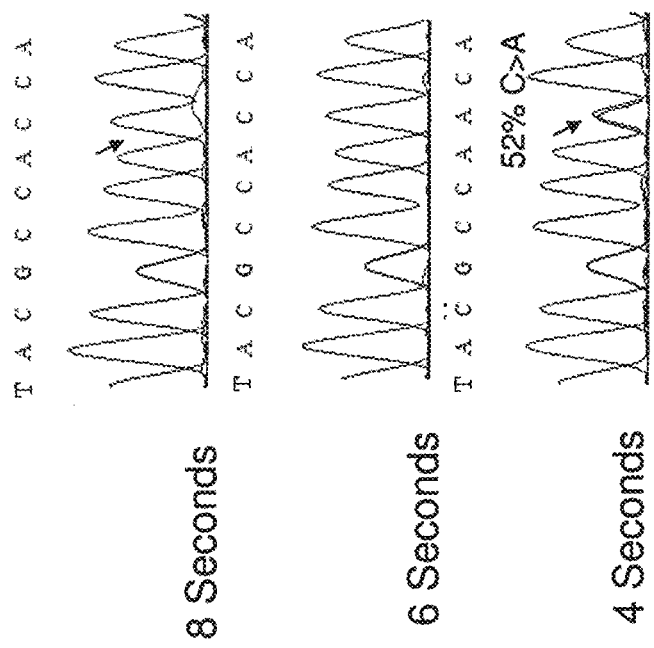
FIG. 2G shows the chromatograms of the LDT-COLD-PCR experiments performed using a denaturation temperature of 89° C. across the indicated limited denaturation times. "HMC"=wild type control; "SW480"=positive mutant control, homozygous for C>A KRAS mutation; "10% p.R273H"=experimental condition, 10% of the total DNA contains the C>A KRAS mutation; "HBKG"=high background.

A 'region of interest' or a 'target region', refers to both the mutant and the wild-type forms in genomic DNA.

A 'target sequence' refers to the sequence that the invention intends to amplify preferentially. Target sequences do not necessarily need to have an exact size, i.e. one may even do a random fragmentation of the genome, or portion thereof, or some other form of restriction digestion prior to hybridization with reference sequence. The target portion that is complementary to the reference sequence will be interrogated for mutations, irrespective of what happens outside the reference sequence portion. This makes things easier, e.g. there is no need for a PCR pre-amplification step to enrich for target sequences from genomic DNA, which may introduce errors. But such enrichment is contemplated according to the invention. If random fragmentation is used, the average fragment size should be at least 10-fold bigger than the target sequences (e.g. large fragments of 1 kb or larger can be interrogated on beads with a reference sequence of 100 bp).

A target sequence refers to a nucleic acid that is less prevalent in a nucleic acid sample than a corresponding wild type sequence. The target may be a mutant target sequence. A mutant target sequence typically makes-up less than 50% of the total amount of wild type sequence+mutant sequence in a sample. The mutant target sequence may be expressed at the RNA and/or DNA level 1:10, 1:15, 1:20, 1:25×, 1:30, 1:35, 1:40, 1:45, 1:50, 1:60, 1:70, 1:80, 1:90, 1:100, 1:150, 1:200× or less than the wild type sequence. For example, a sample (e.g., blood sample) may contain numerous normal cells and few cancerous cells. The normal cells contain non-mutant or wild-type alleles, while the small number of cancerous cells contain somatic mutations. In another embodiment, the target sequence is fetal DNA in a nucleic acid sample obtained from a mother. In this embodiment, the target sequence is present in the fetal DNA while the more prevalent mother DNA contains the wild type sequence. As used herein, a mutant target sequence is meant to include fetal DNA obtained from a pregnant mother. In another embodiment, the invention is directed to detecting one or more methylated alleles in the presence of a large excess of unmethylated alleles, or vice versa in epigenetic analysis. Target sequence and mutant target sequence are used interchangeably herein.

The mutant target sequence is about 17-2000 nucleotides long. In one embodiment the mutant target sequence is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Mutant target sequences share at least 50%, 60%, 70%, 80%, 85%, 90%, 91%, 92%, 93%, 94%, 95%, 96%, 97%, 98%, 99% or more homology to the corresponding wild type sequence, but differs by at least one nucleotide from the wild type sequence. Mutant target sequences according to the invention can be amplified via PCR with the same pair of primers as those used for the wild type sequence.

'Enriching a target sequence' refers to increasing the amount of a target sequence and/or increasing the ratio of target sequence relative to the corresponding reference sequence (typically wild type sequence) in a sample. For example, where the ratio of mutant sequence to wild type sequence is initially 5% to 95% in a sample, the mutant sequence may be preferentially amplified in an amplification reaction so as to produce a ratio of 70% mutant sequence to 30% wild type sequence. Thus, there is a 14 fold enrichment of the mutant sequence relative to the wild type sequence in this hypothetical example. Generally, enrichment of a mutant target sequence results in a 2× to 200× increase in the mutant target sequence relative to the wild type sequence prior to enrichment. The enrichment of the mutant target sequence is at least a 2×, 3×, 4×, 5×, 6×, 7×, 8×, 9×, 10×, 15×, 20×, 25×, 30×, 35×, 40×, 45×, 50×, 60×, 70×, 80×, 90× 100×, 150×, 200× or more fold enrichment. Enrichment of a mutant target sequence results in a sample having 10%, 15%, 20%, 25%, 30%, 35%, 40%, 45%, 50%, 55%, 60%, 65%, 70%, 80%, 90%, 95% or more, mutant target sequence compared to wild type sequence (e.g., 10% mutant target sequence: 90% wild type sequence to 95% mutant target sequence: 5% wild type sequence).

A 'wild type sequence' refers to a nucleic acid that is more prevalent in a nucleic acid sample than a corresponding mutant target sequence (e.g., same region of gene but different nucleic acid sequence). The wild type sequence makes-up over 50% of the total wild type sequence+mutant target sequence in a sample. The wild type sequence can be expressed at the RNA and/or DNA level 10×, 15×, 20×, 25×, 30×, 35×, 40×, 45×, 50×, 60×, 70×, 80×, 90×100×, 150×, 200× or more than the mutant sequence. For example, a sample (e.g., blood sample) may contain numerous normal cells and few cancerous cells. The normal cells contain non-mutant or wild-type alleles, while the small number of cancerous cells contain somatic mutations. As used herein, a "wild type strand" refers to a single nucleic acid strand of a wild type sequence. The term 'wild-type' typically refers to the common polynucleotide sequence or allele for a certain gene in a population. Generally, the wild-type allele will be obtained from normal cells.

The wild type sequence is about 17-2000 nucleotides long. In one embodiment the wild type sequence is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Wild type sequences will share at least 50%, 60%, 70%, 80%, 85%, 90%, 91%, 92%, 93%, 94%, 95%, 96%, 97%, 98%, 99% or more homology to the corresponding mutant target sequence, but will differ by at least one nucleotide from the mutant target sequence. In many embodiments, wild type sequences according to the invention can be amplified by PCR with the same pair of primers as that used for the mutant sequence.

'Allele' refers to alternative forms of a gene, portion thereof or non-coding region of DNA that occupy the same locus or position on homologous chromosomes that have at least one difference in the nucleotide sequence. The term allele can be used to describe DNA from any organism including but not limited to bacteria, viruses, fungi, protozoa, molds, yeasts, plants, humans, non-humans, animals, and archaebacteria. The alleles may be found in a single cell (e.g., two alleles, one inherited from the father and one from the mother) or within a population of cells (e.g., a wild-type allele from normal tissue and a somatic mutant allele from diseased tissue).

An allele can be 17-2000 nucleotides long. In one embodiment the allele is 20, 30, 40, 50, 60, 70, 80, 90, 100, 110, 120, 130, 140, 150, 160, 170, 180, 190, 200, 250, 300, 350, 400, 450, 500, 600, 700, 800, 900 or more nucleotides long. Alleles will generally share 50%, 60%, 70%, 80%, 85%, 90%, 91%, 92%, 93%, 94%, 95%, 96%, 97%, 98%, 99% or more homology to each other. In some embodiments, alleles according to the invention can be amplified by PCR with the same pair of primers as that used for the mutant or the wild-type sequence.

In one embodiment, the present invention is used to enrich a polymorphism. Any given gene may have none, one, or many allelic forms (polymorphism). Common mutational changes which give rise to alleles may be the result of natural or artificial (e.g., chemical carcinogens) deletions, additions, or substitutions of nucleotides. Each of these types of changes may occur alone, or in combination with the others, one or more times in a given sequence.

The term 'mutant' refers to a nucleotide change (i.e., a single or multiple nucleotide substitution, deletion, insertion, or methylation) in a nucleic acid sequence. A nucleic acid which bears a mutation has a nucleic acid sequence (mutant allele) that is different in sequence from that of the corresponding wild-type polynucleotide sequence. The methods of the invention are especially useful in selectively enriching several or numerous mutant alleles simultaneously. The mutant alleles can contain between 1 and 500 nucleotide sequence changes. A mutant allele may have 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400 or 500 nucleotide sequence changes compared to a corresponding wild-type allele. Typically, a mutant allele will contain between 1 and 10 nucleotide sequence changes, and more typically between 1 and 5 nucleotide sequence changes. The mutant allele will have 50%, 60%, 70%, 80%, 85%, 90%, 91%, 92%, 93%, 94%, 95%, 96%, 97%, 98%, 99% or more homology to the wild-type allele. Generally, the mutant allele will be obtained from diseased tissues or cells and is associated with a disease state.

As used herein the term 'melting temperature' or 'Tm' refers to the temperature at which a polynucleotide dissociates from its complementary sequence. Generally, the Tm may be defined as the temperature at which one-half of the Watson-Crick base pairs in a duplex nucleic acid molecule are broken or dissociated (i.e., are 'melted') while the other half of the Watson-Crick base pairs remain intact in a double stranded conformation. In other words, the Tm is defined as the temperature at which 50% of the nucleotides of two complementary sequences are annealed (double strands) and 50% of the nucleotides are denatured (single strands). Tm, therefore defines a midpoint in the transition from double-stranded to single-stranded nucleic acid molecules (or, conversely, in the transition from single-stranded to double-stranded nucleic acid molecules).

The Tm can be estimated by a number of methods, for example by a nearest-neighbor calculation as per Wetmur 1991 (Wetmur, J. G. 1991. DNA probes: applications of the principles of nucleic acid hybridization. Crit Rev Biochem MoI Biol 26: 227-259, hereby incorporated by reference) and by commercial programs including Oligo™ Primer Design and programs available on the internet. Alternatively, the Tm can be determined though actual experimentation. For example, double-stranded DNA binding or intercalating dyes, such as ethidium bromide or SYBR-green (Molecular Probes) can be used in a melting curve assay to determine the actual Tm of the nucleic acid. Additional methods for determining the Tm of a nucleic acid are well known in the art and described herein.

The "preferential denaturation time" or (tp) refers to a window of time, at or above a given temperature during which a duplex having a first Tm and comprising a target sequence strand melts prior to, and preferentially to, reference sequence duplex or wild-type duplex having a second Tm which is higher than the first Tm. The given temperature(s) may be at or above the second Tm according to the invention. The duplex comprising the target sequence strand may be a homo-duplex of a target sequence or may be a hetero duplex of the target sequence and the wild type sequence (or reference oligonucleotide). The reference sequence duplex may be a wild-type sequence duplex or a wild type sequence:reference oligonucleotide duplex. The reference sequence duplex may be a reference oligonucleotide duplex.

As used herein, the term "critical hybridization temperature" (CHT) refers to the temperature (or range of temperatures) over which the rate of hybridization of a wild type DNA target strand with the (immobilized) wild type complementary strand is higher than the rate of hybridization of a mutant DNA target strand with the (immobilized) wild type complementary strand. When there is a single base pair difference between mutant target sequence and reference sequence, there is a reduction in hybridization efficiency relative to a wild type target sequence hybridizing to a fully matched reference sequence. Thus, at the critical hybridization temperature, there is selective formation of wild-type homo-duplexes relative to formation of mutant sequence/wild-type hetero duplexes. The critical hybridization temperature is not the same as the critical denaturation temperature.

Unlike the critical denaturation temperature which generally has a narrow range (typically 0.5-2° C. below Tm), the critical hybridization temperature (CHT) has a broad range. Typically the critical hybridization temperature is a range of different temperatures below the Tm of the wild type strand, and allows differential hybridization of the mutant and wild type target sequences. In some embodiments, the critical hybridization temperature is 0-20° C. lower than Tm. In some embodiments, the critical hybridization temperature is 1-10° C., 2-8° C., or 3-6° C. lower than the Tm of the wild type strand.

It will be understood that the amount of hybridization at a given temperature when hybridizing single strands will be dependent on time. Thus, there also is a limited preferential hybridization time at temperatures below the CHT that will cause preferential hybridization of matched strands.

As used herein, 'reaction mixture' is a mixture suspected of containing a target or mutant sequence duplex that comprises a suitable buffer for allowing the denaturing of a mutant sequence.

The mutant target sequences and wild type sequences are obtained from a biological sample, such as a resected tumor tissue, plasma, and blood. In some embodiments, obtaining mutant target sequences and wild type sequences from a sample involves isolating plasma-circulating DNA from a plasma sample obtained from an individual using the QIAamp MinElute virus spin kit. Obtaining mutant target sequences and wild type sequences from a sample may also involve isolating genomic DNA from the sample followed by fragmentation of the genomic DNA using physico-chemical means or enzyme-driven fragmentation.

As used herein, 'primer pair' refers to two primers that anneal to opposite strands of a mutant target and wild type sequence so as to form an amplification product during a PCR reaction. The primer pair is typically designed so as to have a Tm lower than the Tc of the reaction.

As used herein, "identity" or "homology" refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity.

Percent nucleotide identity can be determined by the default parameters of BLAST. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The comparison window includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An example of an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l Acad. Sci. USA 90:58735787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

In a first aspect, the invention is directed to a method for enriching a target sequence in a nucleic acid sample suspected of having target and reference sequences. The reference and target sequences may be amplified prior to use in the present method. That is the reference and target sequences of interest may be amplified from a genomic template in a PCR reaction prior to use in the present method. An aliquot from this PCR reaction is then transferred for use in the selective enrichment method. Alternatively, the reference and target sequences need not be subjected to a first PCR reaction but can be used in their native form (e.g., genomic DNA) in the selective enrichment method. The target and reference sequences can be obtained from any nucleic acid sequence including, genomic DNA, cDNA, viral DNA, mammalian DNA, fetal DNA or bacterial DNA. (While the reference sequence is generally the wild-type allele and the target sequence is the mutant allele, the reverse may also be true.) The mutant allele may include any one or more nucleotide deletions, insertions or alterations. In some embodiments, the mutant allele is a somatic mutation. In other embodiments, the target sequence is methylated DNA while the reference sequence is un-methylated DNA. Alternatively, the target sequence is un-methylated DNA while the reference sequence is methylated DNA. The primers used in the present method are generally designed so as to produce reference and target sequence amplification products of about 17 to 1000 bases, more preferably about 25 to 500 bases, and most preferably about 50 to 100 bases in size.

The method includes subjecting the amplification reaction mixture to a first denaturing temperature that is above the melting temperature Tm of a reference sequence. The Tm of a nucleic acid can be determined through experimentation or estimated by calculation. The skilled artisan is well aware of numerous well known methods for determining the Tm of a nucleic acid, some of which are described herein. The first denaturing temperature is set according to standard procedures used in PCR. The first denaturing temperature should be sufficiently high and for a sufficient time so as to allow the full denaturation of the target and reference sequences (e.g., 96.degree. C.). In one embodiment, the first denaturing temperature is about 1.degree. C. to 30.degree. C. above the Tm of the reference sequence, more preferably the first denaturing temperature is about 5.degree. C. to 20.degree. C. above the Tm of the reference sequence.

Next, the temperature of the amplification reaction mixture is decreased allowing the target sequences and reference sequences to hybridize. In a preferred embodiment, this hybridization temperature or intermediate temperature is below the first denaturing temperature but above the Tm of the primer annealing/extension temperature (e.g., about 60.degree. C. to 80.degree. C.), and thus allows the target and reference sequences to hybridize while not allowing binding of the primer pair to the target and/or reference sequences. This annealing step results in the formation of hybridization duplexes of double stranded target-target, reference-reference and target-reference sequences.

Next, the target-reference hybridization duplexes are then preferentially denatured by increasing the temperature of the reaction mixture to a temperature that is equal to or higher than the Tm of said reference sequence duplex for a limited time tp causing the preferential denaturation of the target strand/reference strand duplexes of step (b) relative to reference sequence duplexes, to form denatured target strands. Unlike the prior art, the Tm of the reference sequence duplex is met or exceeded, but only for a limited time, whereby the reference-reference sequence duplexes are substantially undenatured. "Substantially undenatured" means at least 60%, preferably at least 70%, more preferably at least 80%, even more preferably at least 90% and most preferably at least 98% undenatured.

After the preferential denaturation of the target-reference (and/or target-target sequence hybridization duplexes), the temperature of the reaction mixture is reduced so as to allow a primer pair to anneal to the target sequence. The annealed primers are then extended by a nucleic acid polymerase, thus enriching the target sequence relative to the reference sequence in the sample.

The steps of the method are generally repeated for multiple cycles in order to get sufficient amplification of the target and reference sequences. In one embodiment, the steps of the method are repeated for 5-40 cycles and more preferably 10-30 cycles. The optimal number of cycles can be determined by one of ordinary skill in the art. Preferably, the present methods are performed in a PCR device, more preferably under real-time reaction conditions in a real-time detection PCR device, such as the SMARTCYCLER real-time PCR device (Cepheid, Sunnyvale, Calif.) and the Mx3005P real-time PCR device (Stratagene, La Jolla, Calif.). In this embodiment, the reaction mixture may include a nucleic acid detection agent (e.g., nucleic acid detection dye such as SYBR Green dye or LC-Green dye or a probe operatively coupled to a fluorescent dye) for quantifying and/or monitoring the amplification products of the reaction. Once the enrichment of the target sequence is complete the sample may be further processed (e.g., for identification of any genetic alterations enriched by the method, e.g., subjected to a sequencing reaction). The enriched reference sequences may be further processed by a variety of procedures including: MALDI-TOF, HR-Melting, Di-deoxy-sequencing, Single-molecule sequencing, pyrosequencing, RFLP, digital PCR and quantitative-PCR.

The foregoing is an explanation of the invention in the context of full COLD-PCR. As summarized above, another aspect of the invention involves application of the invention to fast COLD-PCR. In this aspect, the initial step of melting the duplexes and forming target/reference duplexes is avoided. This can occur when, for example, one starts with a target sequence duplex that has a lower Tm than the reference sequence duplex. According to this aspect of the invention, a method is provided for enriching a target sequence. The method involves subjecting a reaction mixture suspected of having a target sequence (that is part of a target sequence duplex having a first melting temperature (first Tm) and a reference sequence (that is part of a reference sequence duplex having a second melting temperature (second Tm) to a denaturing temperature that is equal to or higher than the second Tm, for a time tp causing the preferential denaturation of the target sequence duplex relative to the reference sequence duplex, wherein said target sequence is at least 50% homologous to said reference sequence. In this manner, target sequences are single stranded and reference sequence are still substantially hybridized. Next, the temperature of the reaction mixture is reduced so as to permit a primer pair to anneal to said target strands. Then the primer pair is extended so as to enrich said target sequence relative to said reference sequence.

The steps of the method are generally repeated for multiple cycles in order to get sufficient amplification of the target and reference sequences. In one embodiment, the steps of the method are repeated for 5-40 cycles and more preferably 10-30 cycles.

In some embodiments, the target sequence is at least 75%, 80%, 85%, 90%, 95% or more than 95% homologous to said reference sequence. In some embodiments, the reference sequence is amplifiable by said primer pair. In some embodiments, the reference sequence is not amplifiable by said primer pair.

In embodiments, tp is that amount causing at least 10% and not more than 95% denaturation of said target strand/reference strand duplexes. In some embodiments, tp is that amount causing at least 25% and not more than 75% denaturation of said target strand/reference strand duplexes.

All of the variations described above in connection with full COLD-PCR are applicable to fast COLD-PCR, including the type of PCR and sequencing equipment that can be used, the dyes, etc. The same is true of ICE COLD-PCR.

As described above, the invention is also useful in connection with ICE COLD-PCR. To combine the advantages of full and fast COLD-PCR in a single format, an ice modification of the COLD-PCR technology has been described. In order to enrich all mutation types, ice-COLD-PCR employs a reference sequence (RS) of a novel-design; the RS is engineered such that (i) it matches the WT-sequence of the anti-sense strand; (ii) PCR primers cannot bind to it; and (iii) it is phosphorylated on the 3'-end so that it is non-extendable by the polymerase. When incorporated into PCR reactions in excess relative to the template, the RS binds rapidly to the amplicons. At a preferential denaturation times, the RS:WT duplexes remain double-stranded, thereby inhibiting selectively the amplification of WT alleles throughout the thermocycling. Conversely, the RS:mutant duplexes are preferentially denatured and amplified. By using a WT-specific RS, all variants can be effectively amplified, regardless of mutational type and position.

In ICE-LDT-COLD-PCR, according to the invention, a melting temperature at or above the Tm of the wild-type amplicon is applied for a limited time (Tp). The steps generally are as follows:
(a) Add the engineered reference sequence (RS) to the reaction mixture, in excess of the template DNA.
(b) Heat (at a high temperature—usually 94° C.) to denature.
(c) Cool (at, for example, 70° C.) to allow hybridization to occur between the RS and the wild-type allele, and between the RS and mutant allele (forming a heteroduplex with one or more mismatches).

(d) Heat-the heteroduplexes will preferentially melt with temperatures at or above the Tm of the wild-type amplicon, when applied for a limited time (Tp). Accordingly, the temperature is adjusted to be at or above the wild-type Tm, and is applied for a limited time to preferentially melt the heteroduplexes.
(e) Cool to allow annealing of primers to the melted strands. (The homo-duplex DNA and wild-type:RS hybrid will remain double stranded and will not be available for primer annealing.
(f) Extend primers-Since the hetero-duplex DNA, denatured, is used as template, a larger proportion of minor variant DNA will be amplified and be available for subsequent rounds of PCR.

The steps of the method are generally repeated for multiple cycles in order to get sufficient amplification of the target and reference sequences. In one embodiment, the steps of the method are repeated for 5-40 cycles and more preferably 10-30 cycles.

In some embodiments, the target sequence is at least 75%, 80%, 85%, 90%, 95% or more than 95% homologous to said reference sequence. In some embodiments, the reference sequence is amplifiable by said primer pair. In some embodiments, the reference sequence is not amplifiable by said primer pair.

In embodiments, tp is that amount causing at least 10% and not more than 95% denaturation of said target strand/reference strand duplexes. In some embodiments, tp is that amount causing at least 25% and not more than 75% denaturation of said target strand/reference strand duplexes.

In any of the embodiments described above and described below, a critical hybridization temperature may be employed such that homo-duplexes (with no mismatches) selectively anneal relative to hetero-duplexes (with mismatches).

The foregoing has included an explanation of the invention in the context of full COLD-PCR, fast COLD-PCR, and ICE COLD-PCR. As described above, other aspects of the invention involve application of Tp to multiplexing COLD-PCR, temperature tolerant COLD-PCR, etc. Some of which will be described in detail below.

In addition, the COLD-PCR methods of the present invention can be used to detect whether methylation has occurred in a target sequence or reference sequence. In a further embodiment, the method utilizes genomic DNA to assay the methylation. The methylation detection method comprises a chemical or enzymatic approach for methylation-sensitive treatment of DNA. Chemical treatments include the incubation of DNA with sodium bisulfite, which selectively converts non-methylated cytosines to uracils. The DNA is first heat-denatured and then can be treated with 5M bisulfite, pH 5-7. Pretreatment of genomic DNA to remove pre-existing uracils is used prior to bisulfite treatment. This pretreatment consists of uracil glycosylase treatment in the presence of 5 mM hydroxylamine, pH 7. The modified DNA may now be used in the methods of the invention.

Because the methylated cytosines of the reference or target sequence are converted to uracils, they will now form mismatches when duplexed with the opposite strand (target or reference), which was not methylated, during they cross-hybridization step of the reaction.

Further aspects of the invention can be described in connection with multiplexing COLD-PCR. It should be understood by those of ordinary skill in the art that certain aspects of the description below applies to other forms of COLD-PCR as well.

According to one form of COLD-PCR multiplexing, a set of specially-designed primer pairs specific to regions of interest are provided. The primer pairs are designed using available computer programs such that upon amplification the resulting amplicons are predicted to have the same melting temperature (i.e., all resulting amplicons are iso-Tm). A number of primer design software are available, and can be used to specially design primers, such as Primer3 (Steve Rozen and Helen J. Skaletsky (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386), Primer-Blast (NCBI tools), Primer Premier (Premier Biosoft International), and OligoPerfect™ Designer (Invitrogen). In some embodiments, primers are designed that upon amplification generate iso-Tm DNA amplicons covering a set of genes shown to correlate with response to a specific drug treatment or a DNA repair pathway.

According to some aspects of the invention, a method for multiplexing COLD-PCR/ice-COLD-PCR to enrich simultaneously several low abundance alleles (mutant target sequences) from a sample is provided. The method involves capturing a reaction mixture suspected of having a mutant target sequence and a wild type sequence within a constrained space. As used herein, 'constrained space' includes, for example, droplets, micro-chambers, pico-litter volumes, emulsion, micro-beads, glass chambers, or alternative solid supports such as a glass-surface or a semiconductor surface. COLD-PCR/ice-COLD-PCR includes a cross-hybridization step, during which mutant sequences hybridize to wild-type sequences to form hetero-duplexed molecules that melt preferentially at a critical denaturation temperature that is below the melting temperature of the homo-duplex. According to the invention, they also melt preferentially when subjecting the duplexes to a temperature that is equal to or higher than the $T_m$ of said reference sequence duplex for a limited time tp causing the preferential denaturation of the target strand/reference strand duplexes relative to reference sequence duplexes, to form denatured target strands. Because proximity of DNA molecules increases the hybridization efficiency substantially, it is expected that performing COLD-PCR in space-constrained small volumes, (e.g. in Raindance™ technologies, FIG. 1, or as in Fluidigm technologies) or on solid support (beads, and in BEAM-ing technologies, glass, or on any other nano-platform) increases greatly the mutation enrichment potential. Therefore the methods described herein may be performed either by solution-based COLD-PCR or by space-constrained COLD-PCR to achieve more efficient and multiplexed mutation enrichment.

The mutant and wild type target sequences may be preferentially enriched prior to capturing the reaction mixture within a constrained space. For example, specially-designed biotinylated capture-oligonucleotides may be used to capture selected fractions from fragmented genomic DNA prior to capturing the reaction mixture within a constrained space. In some embodiments, specially designed molecular inversion probes may be used to capture selected fractions from fragmented genomic DNA prior to capturing the reaction mixture within a constrained space (see, e.g. http://www.ncbi.nlm.nih.gov/projects/genome/probe/doc/Tech-MIP.shtml; Nilsson M et al. Padlock probes: circularizing oligonucleotides for localized DNA detection. Science. 1994 Sep. 30; 265(5181):2085-8). In some embodiments, specially designed microarray-based capture probes may be used to capture selected fractions from fragmented genomic DNA prior to capturing the reaction mixture within a constrained space (Chou et al. DNA sequence capture and enrichment by microarray followed by next-generation sequencing for targeted resequencing: neurofibromatosis type 1 gene as model. Clin. Chem. (2010) 56:1, 62-72). In some embodiments, long-range PCR to selectively amplify the mutant target sequence and the wild type sequence is performed prior to capturing the reaction mixture within a constrained space. In some embodiments, ligation-mediated-PCR of blunted DNA fragments of plasma circulating DNA is performed to preferentially amplify the smaller size apoptotic DNA fragments (FIG. 1B). This type of circulating-DNA amplification increases the proportion of DNA originating from a tumor (Mamon H, Hader C, Li J, et al. Preferential amplification of apoptotic DNA from plasma: potential for enhancing detection of minor DNA alterations in circulating DNA. Clin Chem 2008; 54(9):1582-4).

COLD-PCR/ice-COLD-PCR in Droplets

In some embodiments, the method is performed in droplets (e.g., droplet emulsions). The droplet emulsion may include discontinuous or dispersed regions of a subject fluid (e.g., droplets) in a continuous fluid, with these fluids optionally separated by one or more intermediate fluids. The subject fluid may include, for example, an aqueous solution containing one or more components of interest (e.g., target sequences, beads, fragmented DNA, dNTPs, primers, etc.), and the continuous fluid may be a fluid that is immiscible or slightly miscible with the subject fluid.

The reaction mixture along with PCR reagents is dispensed into droplets. Specially-designed primer pairs specific to the mutant target sequences and the wild type sequences which result in iso-Tm DNA amplicons upon amplification are also dispensed into microdroplets. The droplets containing the fragmented DNA with PCR reagents are then merged with the droplets containing the specially-designed primers such that every microdroplet contains the reaction mixture, primer pair and PCR reagents. The method then includes subjecting the reaction mixture to conventional PCR using the specially designed primers to allow formation of iso-Tm DNA amplicons within all droplets. A typical conventional PCR thermal cycling protocol comprises 30 cycles of (a) denaturation at a range of 90° C. to 95° C., (b) annealing at a temperature ranging from 50° C. to 68° C., and (c) extension at 68° C. to 75° C. In some embodiments, the conventional PCR thermal cycling protocol comprises 5 cycles, 10 cycles, 15 cycles, 20 cycles, 25 cycles, 30 cycles or 35 cycles.

In some embodiments, instead of using specially-designed primer pairs and PCR amplification to generate iso-Tm DNA amplicons, anchor oligonucleotides are used. The anchor oligos are designed such that the resulting DNA strands following extension and ligation are iso-Tm and wherein all the amplicons can be amplified using common primers. Each anchor oligonucleotide comprises a portion that recognizes and binds to the target nucleic acid and a portion that does not bind the target (a non-binding tail). All the forward primers have a tail with a common sequence and all the reverse primers have a tail with a common sequence. Upon merging the droplets containing the reaction mixture with droplets containing the anchor oligonucleotides, the anchor oligonucleotides hybridize to the mutant and wild type target sequences. This is followed by primer extension using dNTPs and Taq DNA polymerase and ligation using DNA ligase. The result is iso-Tm amplicons with common ends formed of the primer tails. The common primer tails enable subsequent COLD amplification of all target DNA sequences in a single reaction, using only a single set of primers which cause the amplification of all the different amplicons.

Next, the method involves performing separate COLD-PCR reactions on millions of droplets in parallel to enrich mutation containing sequences. COLD-PCR reactions employing a limited time Tp can be performed according to the methods described herein.

Even though much of the description herein includes performing methods involving droplets, it should be understood that the methods can be used in the context of other isolated regions of fluids. For example, in some embodiments, isolated regions of fluid may be in the form of subject fluids positioned in one or more wells or reservoirs (e.g., micro-, nano-, or pico-liter sized wells or reservoirs). Thus, where the description herein concerns "droplets", the description may equally apply to other isolated regions of fluids (e.g., fluids in "wells"). In some cases, the subject fluids, while positioned in one or more wells or reservoirs, are not surrounded by an immiscible or slightly miscible fluid. In other cases, subject fluids in the form of droplets can be combined with a well or reservoir system such that the droplets are positioned in the wells or reservoirs during use. Other configurations of isolated regions of fluid are also possible. Additionally, methods involving isolated (e.g., space constrained) components of interest that do not necessarily involve the use of isolated regions of fluids are also possible. For example, in some embodiments, methods described herein can be performed on solid supports (e.g., on glass, beads, or other supports).

Fluids

With respect to a discontinuous or dispersed region of a subject fluid (e.g., a droplet) in a continuous fluid, these fluids can be selected among essentially any fluids (liquids, gases, and the like) by those of ordinary skill in the art by considering the relationship between the fluids. For example, the subject fluid and the continuous fluid may be selected to be immiscible or slightly miscible within the time frame of formation of the dispersed portions. Where the dispersed portions remain liquid for a significant period of time, the fluids may be significantly immiscible. In other cases, the fluids need not be as immiscible (e.g., they may be slightly miscible). Those of ordinary skill in the art can select suitable immiscible or slightly miscible fluids, using contact angle measurements or the like, to carry out the methods described herein.

Various types of fluids may be used in the embodiments described herein. Typically, a subject fluid containing one or more components of interest (e.g., nucleic acids, dNTPs, primers, etc.) is aqueous, although non-aqueous fluids can be used as subject fluids in certain embodiments. If the subject fluid is in the form of a droplet in a continuous fluid, the continuous fluid may be immiscible or slightly miscible with the subject fluid. Non-limiting examples of suitable continuous fluids include oils (e.g., silicone oil, mineral oil), fluorocarbons, hydrocarbons, and non-polar solvents. Sometimes, a continuous fluid, which may be immiscible with the aqueous fluid defining the droplet, is slightly water soluble. For example, oils such as poly(dimethylsiloxane) (PDMS) and poly(trifluoropropylmethysiloxane) are slightly water soluble. Gases such as air may also be used as continuous fluids.

Droplets

Droplets of varying volumes and sizes may be used in the embodiments described herein. In some cases, a method may involve the use of a plurality of droplets having the same or substantially same volume. In other cases, it may be suitable to generate a plurality of droplets having different volumes for use in a method described herein. Volumes of droplets may be chosen depending on the particular application. Generally, a droplet may have a volume between 10 pL and 1 µL, although other volumes are also possible. In certain embodiments, droplets may have volumes of, for example, less than 1 µL, less than 0.1 µL, less than 10 nL, less than 1 nL, less than 0.1 nL, or less than 10 pL. In other embodiments, droplets may have volumes of, for example, greater than 10 pL, greater than 0.1 nL, greater than 1 nL, greater than 10 nL, greater than 0.1 µL, or greater than 1.0 µL. Other ranges of droplet volumes are also possible.

Generally, a droplet may have a size between 0.1 µm and 1,000 µm, although other sizes are also possible. In some embodiments, a droplet has a largest cross-sectional dimension (e.g., a diameter) of, for example, less than 1,000 µm, less than 750 µm, less than 500 µm, less than 100 µm, less than 75 µm, less than 50 µm, less than 25 µm, less than 10 µm, less than 5 µm, less than 1 µm, or less than 0.1 µm. In other embodiments, a droplet has a largest cross-sectional dimension (e.g., a diameter) of, for example, greater than 0.1 µm, greater than 1 µm, greater than 5 µm, greater than 10 µm, greater than 25 µm, greater than 50 µm, greater than 75 µm, greater than 100 µm, greater than 500 µm, greater than 750 µm, or greater than 1,000 µm. Other sizes are also possible.

In some embodiments, a plurality of droplets is substantially monodisperse in size. A plurality of droplets may have a polydispersity of, for example, less than 5%, less than 4%, less than 3%, less than 2%, less than 1.5%, or less than 1%. In other embodiments, the sizes of a plurality of droplets can vary and the droplets are not substantially monodisperse.

The droplets are typically spherical in shape, but may be non-spherical depending on the droplet's surrounding environment. For example, a droplet placed in a well or a channel may take on the shape of the well or channel in some embodiments.

Droplet Formation

The droplets described herein can be formed using any suitable technique. In some embodiments, the droplets are formed by a flow focusing technique. Flow focusing may involve focusing the flow of a subject fluid by exposing the subject fluid to two separate streams of a continuous fluid, and allowing the two separate streams to join and to completely circumferentially surround the subject fluid stream to form a droplet of the subject fluid. In some cases, droplets are formed by flowing a subject fluid through a nozzle. The subject fluid may protrude from the nozzle, and the protrusion may grow as additional subject fluid is injected. Simultaneously, a continuous fluid may be injected to shear the outer surface of the protruding subject fluid, as they are focused into a channel. When the shear on the subject fluid due to the continuous fluid exceeds the surface tension holding the subject fluid protrusion at the nozzle, a droplet of subject fluid is pinched off and dispersed into the continuous fluid. This process repeats and may form droplets of the same size, or of different sizes, depending on the desired mono- or polydispersity of the droplets. Non-limiting examples of methods for forming droplets are described in more detail in U.S. Pat. No. 7,708,949, filed Dec. 28, 2004, entitled "Method and Apparatus for Fluid Dispersion" [Harvard]; International Publication No. WO/2009/139898, filed May 15, 2009, entitled "Valves and Other Flow Control in Fluidic Systems Including Microfluidic Systems" [Harvard]; and U.S. Pat. No. 6,951,632, filed Nov. 16, 2001, entitled "Microfluidic Devices for Introducing and Dispensing Fluids from Microfluidic Systems", each of which is incorporated herein by reference in its entirety for all purposes.

Components of Interest

As described herein, an isolated region of fluid (e.g., a droplet or a fluid in a well) may contain various components of interest. In some embodiments, the components of interest are specific to performing PCR. In some such embodiments, the components of interest are specific to a particular process, such as a COLD-PCR or an ice-COLD-PCR process as described herein.

Certain methods described herein involve the use of a library of different components of interest, such as a library of primer pairs specific to regions of interest which result in iso-Tm DNA fragments upon amplification, or a library of beads comprising different specific capture sequences. In some embodiments, different members of the library (e.g., primer pairs, or beads) may be dispensed into the droplets such that each droplet contains one or more different library members. Each droplet may contain various numbers of copies of a component of interest, as described herein. Multiple droplets can form a droplet library of the components. For example, in one set of embodiments, each droplet contains one primer pair specific to a region of interest which results in a DNA fragment that is substantially iso-Tm with respect to other DNA fragments (contained in other droplets) upon amplification. A plurality of such droplets may form a droplet library of specially-designed primer pairs that result in substantially iso-Tm DNA fragments upon amplification. In another set of embodiments, each droplet contains at least one bead having attached thereto a specific capture sequence. Additionally, each droplet may optionally contain a primer pair, one or more components of which may be attached to the bead or in solution. A plurality of such droplets may form a droplet library of beads with specific capture sequences (optionally with the primer pair). Other examples of libraries of components are provided herein. Each droplet may optionally contain other components of interest (e.g., dNTPs, enzymes, buffer components) that may be generic to the other droplets, and are used for amplification.

In some embodiments, a plurality of droplets is provided, each of the droplets including fragmented DNA of different regions of interest. The region of interest in the droplet may be optionally enriched. In some cases, the regions of interest are enriched prior to being included in the droplets. In other cases, the regions of interest are enriched after being in droplet form. In one set of embodiments, a plurality of droplets is provided, each of the droplets including specially-designed biotinylated capture-oligonucleotides which may be used to capture selected fractions from fragmented genomic DNA. In another set of embodiments, a plurality of droplets is provided, each of the droplets including specially designed molecular inversion probes which may be used to capture selected fractions from fragmented genomic DNA. In another set of embodiments, a plurality of droplets is provided, each of the droplets including specially designed microarray-based capture probes which may be used to capture selected fractions from fragmented genomic DNA. In yet another set of embodiments, a plurality of droplets is provided, each of the droplets including amplified regions of interest (e.g., formed by using long-range PCR). In some embodiments, ligation-mediated-PCR of blunted DNA fragments of plasma circulating DNA is performed to preferentially amplify smaller size apoptotic DNA fragments, and such fragments are included in a plurality of droplets. In yet another set of embodiments, a plurality of droplets is provided, each of the droplets including anchor oligonucleotides. As described herein, the anchor oligonucleotides may be designed such that the resulting DNA strands following extension and ligation are iso-Tm.

Various numbers of copies of a component of interest may be provided in each droplet. For example, in some embodiments, each droplet of a plurality of droplets (e.g., a droplet library) includes a single copy of a component of interest. In other embodiments, each droplet of a plurality of droplets includes 2-5,000 copies of a component of interest (e.g., greater than 2 copies, greater than 10 copies, greater than 50 copies, greater than 100 copies, greater than 200 copies, greater than 500 copies greater than 700 copies, greater than 1,000 copies, greater than 2,000 copies, or greater than 4,000 copies of a component of interest). The component of interest may be those described herein (e.g., DNA fragments, primer pairs, etc.). In some embodiments, each droplet contains on average ~2-1000 genome copies to enable formation of heteroduplexes during COLD-PCR cycling. Other numbers of copies of components of interest are also possible.

In some embodiments a plurality of droplets containing different components of interest (e.g., a droplet library) is provided, the plurality of droplets comprising greater than 2 droplets, greater than 10 droplets, greater than 100 droplets, greater than 500 droplets, greater than 1,000 droplets, greater than 5,000 droplets, greater than 10,000 droplets, greater than 50,000, greater than 100,000, greater than 500,000, or greater than 1,000,000 droplets. As described in more detail herein, a plurality of droplets containing components of interest can be manipulated substantially simultaneously to perform a plurality of reactions in parallel. In certain embodiments, greater than 2 droplets, greater than 10 droplets, greater than 100 droplets, greater than 500 droplets, greater than 1,000 droplets, greater than 5,000 droplets, greater than 10,000 droplets, greater than 50,000, greater than 100,000, greater than 500,000, greater than 1,000,000 droplets can be manipulated substantially simultaneously to perform a plurality of reactions in parallel.

A plurality of droplets containing different components of interest (e.g., a droplet library) may be formed by any suitable method. In some embodiments, a method of forming droplets containing different components of interest involves providing a subject fluid containing the components of interest (e.g., fragmented DNA and reagents for PCR, beads, etc.), and using a flow focusing technique or any other suitable technique to form the droplets. The number of components of interest in each droplet can be controlled by, for example, varying the concentration of the components in the subject fluid prior to droplet formation, by varying the flow rate of the subject fluid and continuous fluid during droplet formation, and/or by using other methods known to those of ordinary skill in the art. Non-limiting examples of methods for producing droplet libraries are described in more detail in U.S. Publication No. 2010/00022414, filed Jul. 17, 2009, entitled "Droplet Libraries" [Raindance™], which is incorporated herein by reference in its entirety for all purposes.

Methods for Merging Droplets

In some embodiments, a droplet of a first type (e.g., a droplet containing a first reagent, which may optionally be a member of a first droplet library) is combined with a droplet of a second type (e.g., a droplet containing a second reagent, which may optionally be a member of a second droplet library). For example, a droplet of a first type may include a first set of components for performing PCR (e.g., COLD-PCR or ice-COLD-PCR, such as fragmented DNA, dNTPs, enzymes such as polymerase and/or buffer components, and a droplet of a second type may include a second set of components for performing PCR (e.g., COLD-PCR or ice-COLD-PCR, such as primers for specific regions). The combined droplet may contain DNA fragments, a specific primer pair and PCR reagents in amounts suitable for a full amplification or enrichment. Optionally, three or more droplets (e.g., droplet containing components for performing PCR) may be combined to form a single droplet in some embodiments. Merging (i.e., fusing) of droplets can be performed by any suitable method. In some embodiments, merging of droplets is performed using an electric field. For example, two streams of droplets in a microfluidic system may combine at an intersection (e.g., in a "Y" configuration) or other suitable configuration, and electrodes that can produce an electric field at or near the intersection may be used to reduce the surface tension of the two droplets. Reduction of the surface tension of the droplets can allow the droplets to merge when the droplets are brought in close proximity to one another. In another embodiment, a heating element can be used to merge droplets. In other embodiments, merging of droplets can be performed by draining the continuous fluid between the two droplets and bringing the two droplets close together. For example, for a device that is fabricated in a polymer such as PDMS, an oil separating the droplets may dissolve into the bulk of the polymer device over time. This can cause the droplets to merge in certain embodiments (e.g., if the droplets or the continuous fluid do not include a surfactant, the droplets are more likely to merge).

In some embodiments, additional regents can be introduced into droplets without the merging of droplets. For instance, a droplet including a fluid of a first type (e.g., a droplet containing a first reagent, which may optionally be a member of a first droplet library) may be combined with a stream of fluid of a second type (e.g., a fluid containing a second reagent).

Other methods for merging droplets or introducing reagents into droplets can also be used. Non-limiting examples of methods for merging droplets and introducing reagents into droplets are described in International Publication No. WO/2007/133710, filed May 11, 2007, entitled "Microfluidic Devices and Methods of Use Thereof" [Raindance™], and Teh et al., "Droplet microfluidics", Lab Chip, 2008, 8, 198-220, each of which is incorporated herein by reference in its entirety for all purposes.

Additives

A variety of different additives can be included in the droplets described herein. In some embodiments, one or more surfactants or detergents may be added to the droplets, and/or to a continuous fluid surrounding the droplets, to stabilize the droplets against coalescence. The type of surfactant chosen may depend on factors such as the type of continuous fluid being used, the contents inside the droplet, and the material containing the emulsion. For example, if the emulsion is contained in a microfluidic device fabricated in a certain material, the surfactant may be chosen such that it stabilizes an aqueous droplet, does not denature the contents inside the droplet, and is compatible with a carrier fluid that does not dissolve in the material used to form the device. Any suitable surfactant, including anionic, non-ionic, or cationic surfactants, may be used. In one set of embodiments, suitable surfactants may include the non-ionic surfactants sorbitan-based carboxylic acid esters ("Span"), including sorbitan monolaurate (Span 20), sorbitan monopalmitate (Span 40), sorbitan monostearate (Span 60) and sorbitan monooleate (Span 80), and perfluorinated polyethers. Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In addition, ionic surfactants such as sodium dodecyl sulfate (SDS) may also be used.

In some embodiments, the droplets include one or more labels. For example, a single droplet may contain a single label in some instances. The label may be attached to an entity inside the droplet such as a chemical or biological material (e.g., fragmented DNA, a primer, a capture sequence) or a non-chemical or biological material (e.g., a bead). In other embodiments, the label is free-floating in the droplet. Any suitable label may be used. Non-limiting examples of labels include optical labels, enzymatic labels and radioactive labels, including but limited to proteins, DNA tags, dyes, quantum dots, radio frequency identification tags, or combinations thereof. The label may be detected by any suitable method such as by fluorescence polarization, fluorescence intensity, fluorescence lifetime, fluorescence energy transfer, pH, ionic content, temperature or combinations thereof.

Wells

In some embodiments, one or more isolated regions of fluid are positioned in one or more wells (e.g., micro-, nano-, or pico-liter sized wells) or reservoirs. As described herein, the isolated regions of fluids may be in the form of droplets, or simply isolated fluids inside the wells. The wells may be configured as a micro-, nano-, or pico-titer plate, positioned in a microfluidic system, or have any other suitable configuration.

A device (e.g., a titer plate, or a microfluidic device) can include any suitable number of wells. For instance, a device can include greater than 1, great than 5, greater than 10, greater than 100, greater than 1,000, greater than 10,000, greater than 50,000, greater than 100,000, greater than 500,000, or greater than 1,000,000 wells that may be used to hold a fluid (e.g., a droplet or other isolated fluid).

The wells may have any suitable size, volume, shape, and/or configuration. For example, a well may have at least one cross-sectional dimension (e.g., a length, width or height) of less than 250 µm, less than 200 µm, less than 150 µm, less than 100 µm, less than 75 µm, less than 50 µm, less than 25 µm, less than 10 µm, or less than 1 µm. In some embodiments, a well can have a volume of less than 50 µL, less than 10 µL, less than 1 µL, less than 100 nL, less than 10 nL, less than 1 nL, less than 100 pL, or less than 10 pL. Other sizes and volumes are also possible.

A well can have any suitable shape for holding a fluid. For example, one well may have a cross-section in the shape of a square, another may be rectangular, and another may have a triangular shape. If the wells are used to contain droplets, different shapes of wells may allow droplets to have different surface energies while positioned in the well, and can cause a droplet to favor one shape over another. Different shapes of microwells can also be used in combination with droplets of different size, such that droplets of certain sizes favor particular shapes of microwells.

In some cases, the size of the well is approximately the same size as the droplet. For instance, the volume of the well can be less than approximately twice the volume of the droplet. This is particularly useful for positioning a single droplet within a single well. In other cases, however, more than one droplet can be positioned in a well. Having more than one droplet in a well can be useful for applications that require the merging of two droplets into one larger droplet, and for applications that include allowing a component to pass (e.g., diffuse) from one droplet to another adjacent droplet. Non-limiting examples of methods for positioning droplets in wells are provided in U.S. Pat. No. 7,556,776, filed Sep. 8, 2005, entitled "Microfluidic Manipulation of Fluids and Reactions" [Brandeis/Harvard]; U.S. Publication No. 2010/0163109, filed Aug. 4, 2009, entitled "Manipulation of Fluids and Reactions in Microfluidic Systems" [Brandeis/Harvard], each of which is incorporated herein by reference in its entirety for all purposes.

It should be understood, however, that in other embodiments, droplets need not be positioned in wells of a microfluidic device. For example, droplets can be aligned side by side one another in a channel or a reservoir of a microfluidic system, each of the droplets separated by a continuous fluid. In another example, a plurality of droplets are positioned (e.g., randomly) in a large reservoir of a microfluidic device. Other configurations are also possible.

Microfluidic Channels

Droplets or other isolated regions of fluid may be positioned in regions of a microfluidic device having any suitable cross-sectional dimension. Typically, fluid channels in a microfluidic system have maximum cross-sectional dimensions of less than 2 mm, and in some cases, less than 1 mm. In some embodiments, all fluid channels of a device have a largest cross sectional dimension of no more than 2 mm or 1 mm. However, larger regions such as reservoirs having a largest cross-sectional dimension of, for example, between 2 mm and 50 mm, may be used to contain droplets or other entities. In one set of embodiments, the maximum cross-sectional dimension of the channel(s) of a microfluidic device are less than 500 microns, less than 200 microns, less than 100 microns, less than 50 microns, or less than 25 microns. The channel can have any suitable cross-sectional shape (circular, oval, triangular, irregular, square or rectangular, or the like), any suitable configuration (e.g., serpentine, straight), and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channels of the device may be hydrophilic or hydrophobic in order to minimize the surface free energy at the interface between a material that flows within the channel and the walls of the channel. For instance, if the formation of aqueous droplets in an oil is desired, the walls of the channel may be made hydrophobic. If the formation of oil droplets in an aqueous fluid is desired, the walls of the channels may be made hydrophilic. Other configurations are also possible.

Methods Involving Microfluidics

As described herein, certain aspects of the invention are directed to methods for enriching simultaneously several low abundance alleles (target sequences) from a sample via COLD-PCR or ice-COLD-PCR. In some cases, the target sequences are mutations at the 1-10% level. A method may involve, for example, introducing a first subject fluid in a dispersed phase in a first channel of a microfluidic device, and introducing a continuous phase fluid in a second channel of the device. The device may include components such as heating and cooling regions for performing PCR. The first subject fluid may include one or more target sequences to be enriched and optionally other components for performing COLD-PCR or ice-COLD-PCR (e.g., dNTPs, enzymes such as polymerase and/or buffer components). The channels of the microfluidic device may be configured to form droplets of the subject fluid (e.g., a first set of droplets); for instance, the channels may be arranged in a flow focusing configuration to allow droplet formation. The method may involve forming a plurality of droplets of the subject fluid (each of the droplets containing fragments of the target sequence to be enriched), the droplets optionally being monodisperse. In some embodiments, the method may involve introducing a second subject fluid containing a second set of components for performing PCR (e.g., primers for specific regions) into the device. The second subject fluid may also be formed into droplets (e.g., a second set of droplets) in some embodiments. In some instances, a droplet from the first set is merged with a droplet from the second set to form combined droplets, each of which contain all of the reagents necessary for performing COLD-PCR or ice-COLD-PCR. The method may involve performing COLD-PCR or ice-COLD-PCR on the plurality of (combined) droplets simultaneously in the microfluidic device to allow simultaneous enrichment of several low abundance alleles (mutant sequences) from the sample.

As a result of performing one or more methods described herein, in some embodiments, a plurality of droplets may be provided, each of the droplets containing enriched fragments of target sequences, wherein the target sequences comprise mutations at the 1-10% level.

The massively parallel COLD-PCR amplification in droplets can be performed by utilizing a micro-fluidic device from RainDance™ Inc. that can dispense DNA and PCR reagents within individual droplets prior to performing amplification on millions of droplets in parallel to enrich mutation-containing sequences. To combine COLD-PCR with RainDance™ technology, the following modifications on the existing Raindance™ technology can be applied:
(a) the amount of input DNA can be adjusted so that each nano-droplet contains an average of ~2-1000 genome copies (instead of an average of 1 genome copy currently applied). In this manner, the formation of heteroduplexes during COLD-PCR cycling will be enabled.
(b) Because RainDance™ amplifies genomic DNA regions with a 10-fold variance from droplet-to-droplet, the total number of droplets formed per experiment can be increased by 5-10-fold. This amounts to increasing the total input DNA used and the total time of droplet formation, e.g. from the current 6-10 minutes to ~60 minutes. In this manner, the probability of capturing low-level events (mutations) in droplets will not be affected by inter-droplet variability, while in the subsequent COLD-PCR step the mutations will be enriched.

COLD-PCR/ice-COLD-PCR on Solid Support

In some embodiments, the method is performed on a solid support. For example, the reaction mixture is captured on magnetic beads. This could be achieved by hybridizing the DNA fragments with biotinylated capture oligos followed by incubating the oligo-DNA hybrids with streptavidin-coated magnetic beads. The beads are then washed to remove unbound DNA. Alternatively, a reference sequence (RS) is attached to a magnetic microbead by streptavidin-biotin binding. The RS is then used to capture the reaction mixture by incubating the RS-bound beads with the reaction mixture. Following incubation and washing, each bead contains several copies of mutant sequences and wild type sequences hybridized to bead-bound RS.

Each bead is then encompassed within an emulsion that contains single bead with captured mutant and wild type sequences and sequence-specific reverse primer bound to it plus common forward primer and PCR mix in solution within emulsion. Conventional PCR is then performed to allow formation of iso-Tm DNA fragments, followed by COLD-PCR reactions within emulsion. In some embodiments, both primers may be common to all target sequences following ligation of common 'tails' to the target sequences, and both primers may be bound to the bead.

In some embodiments, several individual conventional PCR reactions are performed in solution using biotinylated primers with common primer tails. The primer pairs are designed such that all resulting amplicons are iso-Tm (i.e., upon amplification, the resulting amplicons have the same melting temperature). Each PCR product (iso-Tm amplicon) is then incubated with streptavidin-coated magnetic beads. The unbound DNA is removed by washing. This results in several copies of target sequences bound to the surface of the bead (i.e. several groups of ice-COLD-PCR beads with targets bounds to their surface are obtained). All groups of beads are then mixed in a single tube. Each bead is then encompassed within an emulsion so that at most a single bead is enclosed within each emulsion together with PCR components. Using the common primers, COLD-PCR is then performed on all beads simultaneously as described herein.

COLD-PCR/ice-COLD-PCR Bead Compositions

According to some aspects of the invention, a composition comprising streptavidin-coated magnetic microbeads having primer pairs attached to the bead surface are provided. The beads may be 1-3 μm in size. One or both primers specific for the mutant and wild type sequences can be bound to the bead surface. In some embodiments, a sequence-specific primer is attached to the bead, while the common primer is added to the emulsion during amplification. In some embodiments, specially-designed primers that upon amplification result in iso-Tm DNA amplicons are bound to the bead surface.

According to some aspects of the invention, streptavidin-coated magnetic beads having a reference sequence (RS) bound to the bead surface are provided. The reference sequence is specific for the intended DNA target, and may be bound to the bead via a biotinylated nucleotide. Preferably the RS contains a 3'-end di-deoxy-nucleotide with a double biotin held by a carbon-chain spacer. Thus, the RS is 3'-blocked from polymerase extension, and designed according to the methods described in Milbury C A, et al. (Ice-COLD-PCR enables rapid amplification and robust enrichment for low-abundance unknown DNA mutations. Nucleic Acids Res; 39:e2).

The RS can be synthesized by standard oligonucleotide synthesizers. This mode of synthesis has the added advantage that modified nucleotides such as peptide nucleic acid (PNA) or locked nucleic acid (LNA) or uracil (U) can be inserted at will at any position desired on the RS sequence.

Use of PNA at position of the sequence where 'hot-spot' mutations are known to concentrate in clinical cancer samples may boost the ability to enrich these particular mutations. Alternatively, RS can be synthesized via PCR reaction of the appropriate sequence from a wild-type DNA sample. PCR can be conducted with a 5'-biotinylated primer if immobilization to the beads from the 5'-end of the RS is desired. Following PCR, the 3'-end of the synthesized amplicon is blocked from polymerase extension, e.g. by adding a di-deoxy-nucleotide (ddNTP) which prevents further extension. Optionally, the ddNTP is also biotinylated or doubly-biotinylated when it is desirable to enable binding of the synthesized RS to the streptavidin beads from the 3'-end. Another yet way to block the 3'-end is via a —PO4 group, via a C-3 group at the 3'-end of the sequence, or via any other method known to skilled artisans of oligonucleotide synthesis and nucleic acid biochemistry.

RS is complementary to the wild-type DNA target sequence, but 5-20 bp shorter in length so that it does not allow primer binding either to the RS or to the double stranded structure consisting of RS plus a target sequence hybridized to the RS. In some embodiments, the bead also contains on its surface one 5'-biotinylated, bound primer (e.g. a reverse primer) corresponding to one end of the intended DNA target (FIG. 2). The primer has only partial overlap with the RS, and can be designed per the methods described in Milbury C A, et al. (Ice-COLD-PCR enables rapid amplification and robust enrichment for low-abundance unknown DNA mutations. Nucleic Acids Res; 39:e2). The relative amounts of primer-to-RS bound to the surface can be varied, but preferably are in the region of 0.01-100 primer-to-RS ratio; or 0.1-10; or 0.5-2.0. In another embodiment of the invention, a pair of nucleic acid primers corresponding to the ends of the intended DNA target are bound to the ice-COLD-PCR bead.

Figure 3:
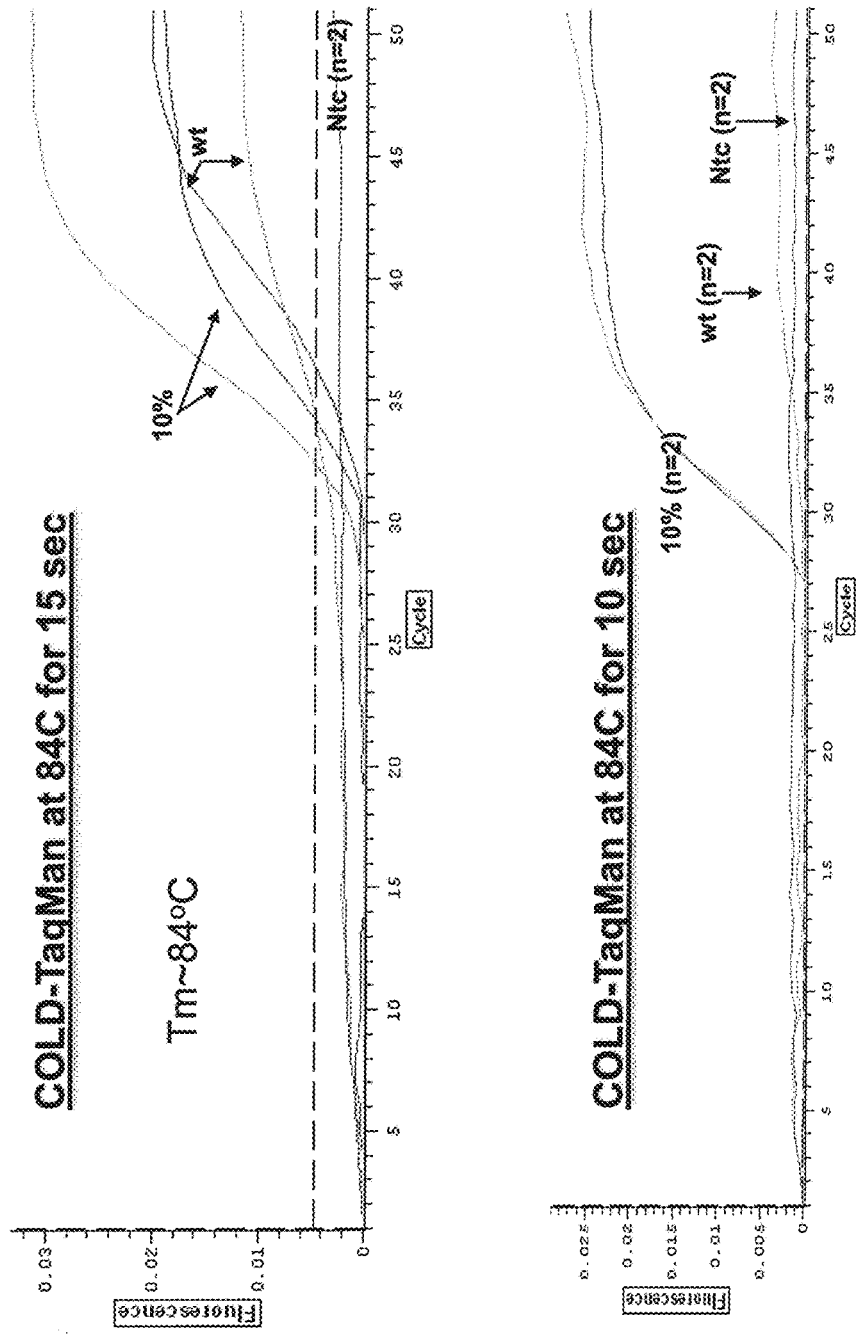
FIG. 3 shows preferential amplification of a mutant EGFR sequence using Taqman-based LDT-COLD-PCR on a BIO-RAD MiniOpticon thermocycler. A mutation-specific Taqman probe was used to detect low-level T790M mutations in EGFR exon 20. The sequences used are the same as those described in (Li J, Wang L, Jänne P, and Makrigiorgos G M. COLD-PCR increases the mutation-detection selectivity of Taqman-based real time PCR. Clinical Chemistry, 2009; 55: 748-756). Limiting the denaturation time increases the discrimination between mutant ("10%") and wild type ("wt") samples. "Ntc"=no template control. For example, by applying a Tm of 84° C. denaturation temperature which is just above the wild type sequence Tm of 83.5° C., one can see a modest difference between mutant and wild type sequences (upper panel, 15 seconds denaturation time). This difference becomes much bigger when the denaturation time is limited to 10 seconds (lower panel), presumably because the mutant sequences have a lower Tm and denature faster than the wild type sequences.
Figure 4:
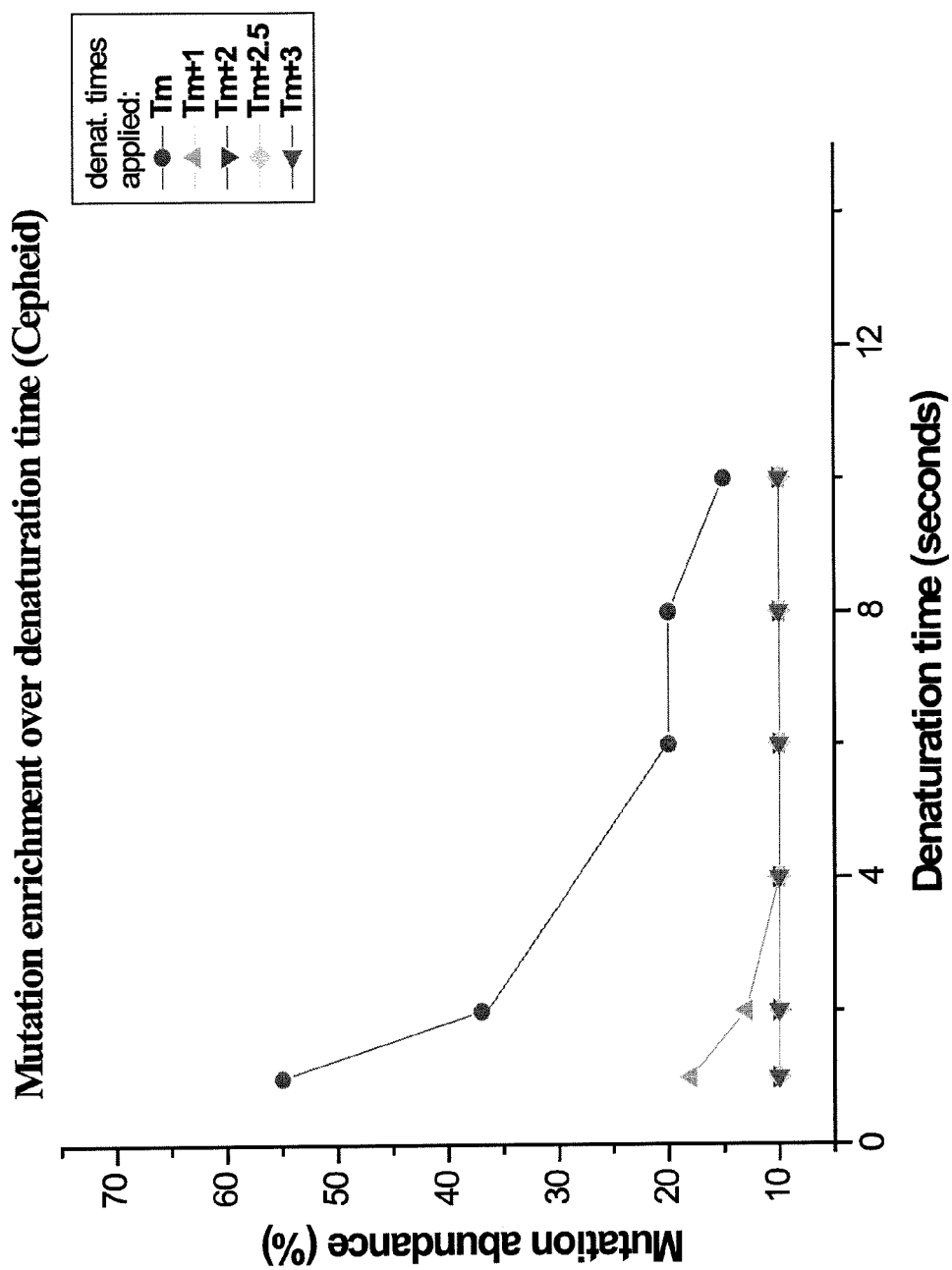
FIG. 4 shows mutation enrichment using LDT-COLD-PCR on a Cepheid thermocycler. A KRAS DNA fragment with Tm=83.5° C. containing 10% initial mutation abundance was amplified using variable denaturation times, and at various temperatures at or above the Tm. The resulting mutation abundance was derived following Sanger sequencing of the LDT-COLD-PCR product. Mutation enrichment is observed over a number of limiting denaturation times and temperatures at or above the Tm. It can be seen that when denaturation times are limited to less than 5 seconds, a substantial enrichment of mutated sequences occurs for denaturation temperatures equal or just above the wild type sequence Tm.

The RS-bound beads described herein perform several functions:
(i) The beads enable sequence-specific capturing and hybridization of target sequences to the corresponding RS on the bead surface when incubated with genomic DNA fragments at an appropriate temperature, e.g. 60-70° C. Following repeated washing of the magnetic beads, each RS-bound bead contains only the target sequences complementary to the capture sequence bound to it. These sequences can be either wild type or mutant sequences, since at hybridization temperatures of 60-70° C. there is little discrimination between wild type and single point mutation-containing target sequences, and both are expected to bind to the RS. Thus, each bead can capture numerous target sequences including both wild type and mutant sequences on its surface, all of which hybridize to the bead-bound RS. In this manner, hundreds or thousands of diverse target sequences can be hybridized simultaneously with their respective RS on the bead surface, hence each RS serves as a 'magnet' for its own complementary target sequence.
(ii) The beads enable performing the subsequent COLD-PCR in emulsion. In some embodiments, following incubation of the RS-bound beads with target sequences and capturing of each group of target sequences on the corresponding bead-bound RS, a forward (common to all target sequences) primer and PCR components are added to the bead solution and the beads are encompassed in emulsion, according to the general protocols described in Diehl F, Li M, He Y, et al. BEAMing: single-molecule PCR on microparticles in water-in-oil emulsions. Nat Methods 2006; 3(7):551-9; Li M, Diehl F, Dressman D, et al. BEAMing up for detection and quantification of rare sequence variants. Nat Methods 2006; 3(2):95-7; and Dressman D, Yan H, Traverso G, et al. Transforming single DNA molecules into fluorescent magnetic particles for detection and enumeration of genetic variations. Proc Natl Acad Sci USA 2003; 100 (15):8817-22. Each emulsion encompasses a RS-bound bead. Following this, the beads contain several copies of captured mutant and wild type sequences, as well as reverse primer bound to their surface, and forward primer in solution within emulsion (FIG. 3). During the subsequent COLD-PCR amplification, captured target sequences that are wild type remain bound to RS; while captured mutant sequences become denatured and become selectively amplified within the emulsion. After amplification the beads contain mainly mutated target sequences, some of which are bound to the bead surface while others are free-floating within the emulsions (FIG. 4). Due to the proximity of DNA strands achieved by performing COLD-PCR within emulsion, high enrichment of mutations at any position of the captured target sequences will be achieved in a multiplex fashion.

Temperature-Independent COLD-PCR

According to some aspects of the invention, instead of generating iso-Tm DNA amplicons prior to initiating COLD-PCR, time-independent COLD-PCR is performed. This modification removes the requirement that the user isolates iso-Tm fragments prior to initiating COLD-PCR, and provides a one-step, one-tube procedure for all genomic DNA fragments or fractions thereof. Therefore the described modification enables multiplex COLD-PCR/ice-COLD-PCR on DNA targets with diverse denaturation temperatures, simultaneously. The approach can be used to perform temperature-independent COLD-PCR (TI-COLD-PCR) either in solution, in droplets or on solid support.

In some embodiments, the reaction mixture is dispensed into droplets which are then merged with droplets containing primers for intended DNA targets. TI-COLD-PCR is performed by ramping the preferential denaturation time from lower to higher values so that the entire range of all possible denaturation times is gradually covered. In other words, as tp is increased at a given temperature or range of temperatures, then duplexes with higher and higher melting temperatures will preferentially denature over their wild type counterparts. In some embodiments, conventional PCR is performed prior to TI-COLD PCR to enrich the low-abundance mutations prior to TI-COLD PCR.

TI-COLD-PCR can be performed, for example, for 10 cycles for one second at 85° C., then 10 cycles for two seconds at 85° C., then 10 cycles for three seconds at 85° C., then 10 cycles for four seconds at 85° C., then 10 cycles for five seconds at 85° C., and so on until all sequences have been denatured at some stage. At all stages and for all sequences, mismatch-containing sequences formed by wild-type:mutant duplexes or mutated sequences that have lower Tm than the wild type sequences, will be preferentially amplified. The incremental changes can be longer, such as for 5 seconds, then 10 seconds, then 15 seconds, 20 seconds, and so on until all sequences have been denatured at some stage. Beyond a certain period of time, all sequences would amplify equally, i.e. the already-enriched mutated sequences plus the wild type sequences would have equal amplification at extended denaturation times for wild-type strands having a Tm of at (or below) a given temperature (86° C. in the example above). At the final (longest) denaturation time, the mutated, amplified target sequences would be enriched over wild type sequences.

TI-COLD PCR can be performed in solution in a tube. This requires that for each target sequence there is a separate primer pair and all primers are added together in the reaction. Thus, the primer pair specific to a given sequence would not be used until the denaturation time is long enough to cause denaturation, where mutant target sequences amplify preferentially over wild-type sequences. At each denaturation time (repeated over a number of cycles), the primers specific for the target sequence would be substantially consumed in synthesizing mainly the mutant amplicons. At longer times, any remaining primers would be used equally for amplifying the (enriched) mutant sequences plus the wild-type, until completely consumed.

However, a problem with this approach is that the primers would tend to react with each other and form primer-dimers and by-products. This unwanted effect can be avoided by limiting the primer concentration to lowest possible (e.g., in the region of 0.01-0.2 μm), attaching to all target sequences the same primer on one end, and a sequence-specific primer on the other end, or attaching common primers to both ends of all target sequences. Alternatively, TI-COLD PCR can performed in a space constrained manner in droplets as performed by Raindance™, or by Biorad Inc, or in nano-volumes as by Fluidigm Inc, or in OpenArray™ format, or on solid support as described herein. For example, by using RS-bound beads that have a target-specific primer bound to their surface and a generic forward primer in solution, each emulsion would contain primers specific to the target sequence captured on the RS, therefore avoiding unwanted primer interactions. Therefore ramping of the time from lower to higher values would amplify the target sequences selectively in all emulsions simultaneously, without the need to isolate iso-Tm DNA targets or to know a-priori the required Tm for COLD-PCR. In some embodiments, conventional PCR is performed prior to TI-COLD PCR to enrich the low-abundance mutations prior to TI-COLD PCR.

Temperature-Independent COLD-PCR on Solid Support

Beads are encompassed in an emulsion, each bead containing immobilized on its surface (a) reference sequence 1 for target 1, (b) forward primer 1 for target 1. The emulsion also contains (c) reverse primer 1 for target 1, polymerase, dNTP and PCR buffers. Additionally, emulsions 2, 3, 4, etc. similarly contain components for targets 2, 3, 4, etc. The primers are provided within each emulsion in limited quantity, and the primers may be exhausted after about 20-25 cycles. Assume that target 1 has a Tp=5 seconds at 86.0° C., target 2 has Tp=10 seconds at 86.0° C. and target 3 has a Tp=15 seconds at 86°, etc. ice-COLD-PCR is first applied for 20 cycles at Tp=5 seconds for target 1, during which mutation-containing sequences in emulsion containing target 1 are amplified, while wild-type sequences are not amplified. At the same time, none of the targets 2, 3, etc. will amplify in other emulsions, as neither wild type nor mutant sequences denature at this denaturation temperature. Following the 20 cycles of ice-COLD-PCR, the primers are exhausted and the reaction within emulsion containing target 1 stops. If additional targets within different emulsions have a Tp similar to that of target 1, then they will also amplify at this temperature, similar to target 1. In this way, all Iso-Tm fragments co-amplify at Tp=5 seconds at 86° C. for the initial 20 cycles.

The cycling is then switched for another 20 cycles at Tp for target 2 (Tp=10 seconds at 86° C.), during which mutation-containing sequences in emulsion containing target 2 are amplified, while wild-type sequences are practically not amplified. Similarly, following the 20 cycles of ice-COLD-PCR, the primers are exhausted and the reaction within emulsion containing target 2 stops. Targets that also happen to have Tp=10 seconds at 86.0° C. co-amplify with target 2. By following the same scheme, denaturation times spanning all of the targets are covered in a single tube, single COLD-PCR reaction. Reactions in individual emulsions start whenever the correct Tp is reached and stop whenever the primers are exhausted. This approach ensures that the primers are not be prone to create primer dimmers within emulsions. In some embodiments, all targets have common primers on one or both ends. Because many cycles of PCR are applied in this approach, polymerase that does not get easily inactivated at high temperatures can be used (e.g. Phusion).

The major advantage of this approach is that one does not need to isolate iso-Tm fragments from genomic DNA, or even to know what is the Tm of the targets. Because the time is ramped over all possible denaturation times at a selected temperature, starting from shorter to longer times, mutation enrichment occurs always until primers are exhausted within all emulsions. Reactions in individual emulsions start whenever the correct Tp is reached and stop whenever the primers are exhausted.

Temperature-Independent COLD-PCR Using Incorporation of Modified Deoxynucleotides During Amplification.

In some embodiments, temperature independent COLD-PCR of multiple DNA fragments having different Tm is performed in the presence of modified deoxynucleotide triphosphates in the reaction. For example, triphosphates containing modified bases such as: 2'-deoxy-inosine; di-amino-purine; iso-guanine; iso-cytosine; methyl-cytosine; 7-(2-thienyl)imidazo[4,5-b]pyridine; 2-nitro-4-propynylpyrrole; aminoallyl-uridine; xanthine; diaminopyrimidine; metal-coordinated bases such as 2,6-bis(ethylthiomethyl)pyridine with silver ion, or a mondentate pyridine with a copper ion; nitroazole analogues; or any other modified nucleotide triphosphate that can be incorporated into DNA by the polymerase during PCR may be used. By incorporating modified bases into DNA during PCR, the Tm of the various DNA fragments changes. In one example, the polarity of mutation-induced Tm difference may be reversed by using modified nucleotides. Thus, by incorporating deoxy-inosine (I) in the place of deoxy-guanosine, as well as deoxy-di-amino-purine (D) in the place of deoxy-adenine, a Tm-increasing mutation (A>G) is converted to a Tm-decreasing mutation (D>I). Thereby sequences that contain I instead of D can be preferentially amplified using the approaches described in previous sections ('FAST-COLD-PCR' approach).

In another example, the modified dNTPs can be used to make the Tm of different sequences more uniform. Thus, let's assume that a given DNA fragment has a 60% GC content and a corresponding high Tm of 90° C., while a second fragment has a 40% GC content and a corresponding Tm of 85° C. If 2'-deoxy-inosine is incorporated in the amplification reaction, this will replace most guanines in both DNA fragments resulting in the formation of inosine: cytosine bonds instead of G:C bonds. Accordingly, the effect of the GC content on the Tm will be reduced or eliminated and both sequences will end up having similar Tm. In the same way, the opposite approach can also be applied. By incorporating 2'amino-purine in the place of adenine, the Tm of all sequences will increase, thus making a uniform high Tm for all fragments.

Such approaches that utilize modified DNA bases will make easier the operation of TI-COLD-PCR, as the Tm of numerous DNA fragments can be brought closer to each other. When this occurs, then the Tp also can be a narrower window and easy to accomplish.

Electrophoretic Techniques to Separate DNA Fragments According to their Tm

In some embodiments, instead of specially-designed primer pairs and PCR amplification to generate iso-Tm DNA fragments, electrophoretic techniques are used to separate DNA fragments according to their Tm. Diverse DNA targets with a range of different Tm are physically separated by gel or capillary electrophoresis and collected in different fractions, each fraction having diverse DNA targets that have essentially the same Tm. For example, in CDCE (constant denaturant capillary electrophoresis, Khrapko et al. Nucleic Acids Res. 1994 Feb. 11, 22(3):364-369) double stranded DNA fragments are injected through a capillary subjected to a gradient of temperatures. DNA that denatures at a certain Tm1 travels at a different rate through the capillary from non-denatured DNA and therefore separates from double stranded DNA and can be collected as fraction 1. Similarly, DNA that denatures at Tm2 is collected at fraction 2, etc. Each fraction contains DNA targets with diverse sequences, all of which have the same (or very similar) Tm.

Other approaches for physical separation of iso-Tm diverse DNA fragments include gel electrophoretic means, such as denaturing gradient gel electrophoresis (DGGE), constant denaturant gel electrophoresis (CDGE), temperature gradient gel electrophoresis (TGGE) and temperature gradient capillary electrophoresis (TGCE).

Analyzing the COLD-PCR-Amplified Sequences

Sequencing:

Following enrichment of mutation-containing target sequences via the multiplex COLD-PCR-based approaches and compositions described herein, the amplified DNA fragments can be pooled together by dissolving the emulsion (or by simple purification if the reaction was performed in solution without emulsion) and processed for sequencing by any one of the next generation sequencing (NGS) approaches available, including second and third (single molecule) sequencing technologies. Several NGS approaches incorporate a PCR step as part of the sequencing. Accordingly, one approach is to take advantage of this PCR step and incorporate the COLD-PCR process within the sequencing itself.

Incorporation of COLD-PCR within the 'PCR-Colony' Amplification Step Used in Next Generation Sequencing:

This approach, integrates COLD-PCR within the actual sequencing itself, as opposed to the previous examples that describe iso-Tm COLD-PCR or TI-COLD-PCR that is performed as an independent procedure prior to NGS.

During next generation sequencing, the target DNA is immobilized on solid support and PCR-amplified clonally to form PCR-Colonies (also known as 'Polonies'), following which sequencing on solid support takes place. The present invention enables the simultaneous amplification of numerous iso-Tm fragments on solid support using COLD-PCR. Because of the proximity of targets immobilized on solid support, COLD-PCR is expected to be highly efficient, essentially amplifying only mutation-containing sequences which are then directly sequenced. Thereby the efficiency of next generation sequencing is predicted to increase by several orders of magnitude since essentially ONLY mutation containing sequences are read. Essentially this provides next generation sequencing of mutant-only DNA.

Iso-Tm COLD-PCR on Solid Support, as Part of Polony-Formation Step within Next Generation Sequencing.

A. Aimed Towards the Illumina Platform.

1. iso-Tm fragments are made from genomic DNA, using one of the methods described herein. Fragmentation is not performed randomly, and the result is single-stranded targets with common adaptors.
2. Target DNA is bound randomly to the inside surface of the flow cell channels.
3. Nucleotides and polymerase is added to initiate solid-phase bridge full-COLD-PCR amplification of iso-Tm fragments.
4. Full-COLD-PCR on solid support will allow denaturation of mismatch-containing sequences formed by hybridization of immobilized mutant sequences with adjacent immobilized wild-type sequences, while non-mismatched sequences (wild type) will be effectively suppressed.
5. Denatured sequences contain a high percent of mutation-containing sequences
6. Dense clusters of double-stranded DNA enriched in mutation-containing sequences are generated in each channel of the Illumina flow-cell.
7. This is followed by sequencing-by-synthesis, according to the Illumina platform.

B. Aimed Towards the Roche-454 Platform, or the Ion Torrent System (PCR in Emulsion)

1. Make iso-Tm fragments from genomic DNA, using one of the methods described herein. Fragmentation is not performed randomly, and the result is single-stranded DNA targets. In some embodiments, the targets contain common adaptors.
2. Bind target DNA to beads containing dense primers on their surface, each primer specific for a different target. In some embodiments, the primers recognize the common adaptors.
3. Mix targets with beads at a ratio of less than 1 target per bead, then enclose beads in emulsion together with nucleotides, polymerase and one of the two primers that are also immobilized on the bead as per the Roche-454 protocol.
4. Initiate emulsion-based full-COLD-PCR amplification of iso-Tm fragments. Full-COLD-PCR immobilized on beads enclosed in nano-reactors (emulsion) enables rapid hybridization of mutant with wild type sequences that allows denaturation of adjacent immobilized wild-type sequences.

BEAM and Flow-Cytometry:

It may be desirable to isolate beads/emulsions that contain mutated sequences that have been amplified during COLD-PCR, and discard beads that contain only wild type sequences, in order to make subsequent sequencing even more efficient. In the case where iso-Tm sequences have been first isolated from genomic DNA prior to COLD-PCR, one expects that the only emulsions containing copious DNA amounts are those that include mutated sequences, since in the emulsions with wild-type sequences there will be little amplification. In this case, beads with amplified DNA can be sorted via high throughput flow-cytometry in the presence of DNA-binding dye, in an approach similar to BEAM technology (see Li M, Diehl F, Dressman D, et al. BEAMing up for detection and quantification of rare sequence variants. Nat Methods 2006; 3(2):95-7). The population of beads that produce strong fluorescence signals is the one that contains amplified mutated sequences and can be sorted and sequenced.

REpeated DNA-Strand SEparation at Critical Denaturation Temperatures (RE.SE.CT), Also Known as Differential Strand Separation at Critical Temperature (DiSSECT).

According to one aspect of the invention, a method that enables identification of variant-sequence alleles (mutant target sequences) in the presence of a large excess of non-variant alleles (wild type target sequences) in nucleic acids without the complication of polymerase-introduced errors or other primer-introduced artifacts is provided. The enrichment that can be obtained via PCR-based methods has a limit, since after several cycles of synthesis the polymerase unavoidably introduces mis-incorporations (PCR errors) that are subsequently scored as mutations. Repeated PCR/COLD-PCR can also introduce mis-priming that results to amplification of unwanted non-target sequences. Furthermore, there are powerful genetic analysis methods currently emerging ('third generation sequencing') that may obviate the use of PCR altogether.

RE.SE.CT allows the enrichment of mutant target sequences without introducing mis-incorporations, and amplifies preferentially minority alleles from mixtures of wild type and mutation-containing sequences, irrespective where the mutation lies, thereby providing a high enrichment of the mutated sequences without PCR and without introducing any artifacts. RE.SE.CT exploits the observation that double stranded DNA sequences containing one or more single base mismatches denature fast and re-associate slowly relative to fully-matched sequences. By reducing the denaturation time to a value appropriate for discriminating between fully matched wild type sequences and mismatch-containing mutated sequences, mutations at any position along the sequence are enriched during RE.SE.CT. Subsequently the enriched sequences can be screened with any of the currently available methods for detecting mutations, including Sanger Sequencing, high resolution melting (HRM), SSCP, next generation sequencing, and MALDI-TOF.

The method can be used for multiplexed detection of DNA methylation, and for enriching mutant DNA strands, and damaged DNA strands, such as DNA containing abasic sites that result from exposure to DNA damaging agents. The abasic site position would create a mismatch upon hybridization to the reference sequence, thus enabling its selective denaturation upon RE.SE.CT. Unlike with ice-COLD-PCR-based applications that require DNA polymerase to operate, in RE.SE.CT the 3' end of RS does not need to be blocked, as long as no polymerase is used in the mutation enrichment process. One advantage of this approach is that it is easy to synthesize the reference sequence using a simple PCR reaction rather than synthesis on oligonucleotide synthesizers which is expensive. This allows also larger reference sequences to be used, e.g. 200 bp RS. This is a substantial advantage over COLD-PCR.

In another aspect of the invention, a method for preparing a single stranded mutant target sequence from a mixture of target sequences suspected of containing both the mutant target sequence and a wild type target sequence is provided. The method involves using a critical hybridization temperature in combinatio9n with the COLD-PCR methods described herein. In this aspect, a mixture containing single stranded mutant sequences and single stranded wild type sequences is formed. The mixture is then contacted with an excess references sequence that is complementary to the wild type sequence, and a complete hybridization steps is performed, i.e., the temperature is reduced to permit formation of target strand/reference strand duplexes, wherein the duplexes include mutant strand/reference strand duplexes and wild type strand/reference strand duplexes. Next, a selective denaturation step is performed, i.e., subjecting the mixture having a mutant/reference sequence duplex having a first melting temperature (first $T_m$) and a wild-type/reference sequence duplex having a second melting temperature (second $T_m$) to a denaturing temperature that is equal to or higher than the second $T_m$, for a limited time tp causing the preferential denaturation of the target sequence duplex relative to the reference sequence duplex. In some embodiments, the wild type strand/reference strand duplexes formed by selective denaturation are removed. Optionally, in some embodiments, the complete hybridization step, the selective denaturation step, and the removal of the wild type strand/reference strand duplexes formed by selective denaturation are repeated at least 1, 2, 3, 5, 10, 50, 75, 100, 200, 300, 400, 500, 600, 700, 800, 900, or 1000 times. In some embodiments, additional excess of reference sequence is added after the removal of the wild type strand/reference strand duplexes.

Optionally, in some embodiments, the method further comprises performing a selective hybridization step, i.e., the temperature is reduced to a critical hybridization temperature to permit selective formation of wild-type target sequence/reference sequence duplexes relative to formation of mutant sequence/reference sequence duplexes. In some embodiments, the selective denaturation and selective hybridization steps are repeated at least 1, 2, 3, 5, 10, 50, 75, 100, 200, 300, 400, 500, 600, 700, 800, 900, or 1000 times to further enrich for the single stranded mutant target sequences.

Optionally, in any of the foregoing embodiments, the reference sequences are attached to particles. Optionally, in any of the foregoing embodiments, the reference sequences are attached to magnetic particles.

Optionally, in some embodiments, the target sequences are contacted with an excess of at least two different reference sequences, each different reference sequence being complementary to a different wild-type target sequence, and the duplexes formed by the wild type sequences/reference sequences having substantially the same melting temperature, and/or substantially the same Tp at a given temperature. In some embodiments, the target sequences are contacted with an excess of at least 10, 15, 20, 30, 40, 50, 100, 200, 500, or 1000 different reference sequences.

Optionally, in some embodiments, the method further comprises detecting the single stranded mutant target sequences. Optionally, in some embodiments, the method further comprises isolating the single stranded mutant target sequences.

In some embodiments, the single stranded mutant target sequences are isolated by contacting the single stranded mutant target sequences with primers (see, e.g., FIG. 12 of U.S. Patent Publication No. 20110217714). The temperature is then is rapidly lowered to 50-55° C. to allow binding of primer to those sequences that are single stranded. The temperature is raised to 65-70° C. to enable single primer extension via a polymerase, in the presence of tagged dNTPS. The result is that mutant sequences selectively obtain a tagged complementary sequence. Following this, the tagged sequences are immobilized on solid support coated with a capture moiety, and the non-tagged DNA (which is mainly wild-type DNA) is removed. The single-stranded, mutated sequences are then recovered from the solid support, for example, by thermal denaturation at 95° C. The mutated sequences that are recovered represent the original DNA target template, not the template generated via the polymerase extension—which is tagged and stays bound to the solid support after denaturation. In some embodiments, the tag moiety is biotin, and the capture moiety is avidin, or vice versa.

Alternatively, in order to selectively tag the single stranded mutant sequences, one could use a tagged primer, instead of adding tagged dNTP to the solution. In some embodiments, the tag moiety is biotin, and the capture moiety is avidin, or vice versa.

In some embodiments, the single stranded mutant target sequences are isolated by adding an excess of tagged reference sequences (see e.g., FIG. 13 of U.S. Patent Publication No. 20110217714). The temperature is then rapidly reduced to below 50° C. to permit formation of single stranded mutant target sequence/tagged reference sequence duplexes. In the next step the excess reference probe is eliminated, for example, by exonuclease treatment, and the tagged sequences are captured on a support coated with a capture moiety. The single-stranded, mutated sequences are then recovered from the solid support, for example, by thermal denaturation at 95° C. In some embodiments, the tag moiety is biotin, and the capture moiety is avidin, or vice versa.

In some embodiments, the single stranded mutant target sequences are isolated by contacting the formed duplexes with an excess of non-tagged adaptor and thermostable ligase at critical hybridization temperature (e.g. 78° C.). The non-tagged adaptor preferentially ligates to double-stranded templates. In this way, the non-tagged adaptor will ligate selectively to the wild type alleles, since these are in duplexes with the reference sequences (see e.g., FIG. 14 of U.S. Patent Publication No. 20110217714), but not to mutant alleles since these are mainly single-stranded. Next, a tagged adaptor that is in high excess over the previously added, non-tagged adaptor is used and the temperature is reduced rapidly so that the target DNA binds to reference sequence and tagged adaptor ligates to all remaining double stranded sequences (that would be expected to be mainly mutant sequences, since the majority of wild type sequences was ligated to a non-tagged adaptor). Subsequently tagged sequences are captured on support coated with a capture moiety. The single-stranded, mutated sequences are then recovered from the solid support, for example, by thermal denaturation at 95° C. In some embodiments, the tag moiety is biotin, and the capture moiety is avidin, or vice versa.

In some embodiments, the single stranded mutant target sequences are isolated by using tagged reference sequences. The duplexes formed by wild type sequence/tagged reference sequence are removed by capture on solid surface coated with a capture moiety, thereby leaving an enriched population of single-stranded mutant target sequences. In some embodiments, the tag moiety is biotin, and the capture moiety is avidin, or vice versa.

In some embodiments, the single stranded mutant target sequences are isolated by using reference sequences attached to magnetic beads. After performing the selective denaturation step, that permits selective denaturation of mutant strand/reference strand duplexes, but not the wild type strand/reference strand duplexes, the magnetic beads are removed, thereby resulting in the removal of all reference sequences plus any duplexes formed with the reference sequences. In some embodiments, additional excess reference sequence attached to magnetic beads is added, and the process is repeated at least 1, 2, 3, 5, 10, 50, 75, 100, 200, 300, 400, 500, 600, 700, 800, 900, or 1000 times. The reference sequence can be bound through the 5' or the 3' end on magnetic beads, and magnets can be turned on and off to enable repeated removal of magnetic beads from the reaction, following selective denaturation of mutated sequences. Size of reference-sequence-bound-beads (RS-beads) can vary from large (5 micrometers) to small (nanometers diameter). (see e.g., FIG. 15 of U.S. Patent Publication No. 20110217714)

In some embodiments, the target sequences are pre-amplified using asymmetric PCR prior to contacting with the reference sequences. Asymmetric PCR preferentially amplifies one DNA strand in a double-stranded DNA template, and is routinely used in sequencing and hybridization probing where amplification of only one of the two complementary strands is required. PCR is carried out as usual, but with a great excess of the primer for the strand targeted for amplification. Because of the slow (arithmetic) amplification later in the reaction after the limiting primer has been used up, extra cycles of PCR are required.

In some embodiments, the target sequences are contacted to the reference sequences in the presence of an organic solvent. Organic solvents present during the binding of interrogated target sequences to the reference sequences can have beneficial effects. For example, solvents like betaine, DMSO, formamide and others enhance the hybridization fidelity of nucleic acids. As a result, the Tp for a perfectly matched wild-type sequence and a mutation-containing sequence is exaggerated in the presence of organic solvents. In addition, the melting temperature (Tm) is reduced when organic solvents are present, thus enabling RE.SE.CT to operate at lower temperature that are easier to achieve and that avoid potential temperature-caused damage to the DNA strands. At the same time, DNA fragments with substantially different DNA melting temperatures in regular aqueous buffer end up with melting temperatures that are closer to each other when organic solvents are used, thus making multiplexing easier. Organic solvents as much as 50% or higher can be used during RE.SE.CT since there is no enzyme involved in the process and as a result the organic solvent does not inhibit any part of the process.

RE.SE.CT can be used in conjunction with COLD-PCR, in order to increase even further the mutation enrichment obtained via COLD-PCR. Therefore one may envision COLD-PCR to enrich mutated sequences by 10-fold; then the sample is used for RE.SE.CT to enrich mutated sequences by another 10-fold; and so on. In this way COLD-PCR and RE.SE.CT act synergistically to increase the mutation enrichment. RE.SE.CT may also be used in conjunction with different amplification methods, e.g. with isothermal amplification well known in the art, such as LAMP, SPIE, etc.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Experimental Design

The present invention was validated across three PCR platforms (Examples 1-3). For each experiment, the genomic sample containing the sequences to be amplified was comprised of roughly 90% wild-type (reference) sequence, and 10% mutant Kras (containing a C>A mutation) or 10% mutant EGFR (containing T790M mutation) (target) sequences. Each platform was tested across various denaturation temperatures, at various limited denaturation times. Sequencing was performed on the Kras PCR products to determine the relative enrichment in mutant (target) Kras sequence that was amplified, as compared to amplified wild-type (reference) sequence; a Taqman-based protocol was applied to observe enrichment in mutant (target) EGFR sequence.

Materials and Methods
Source of Genomic DNA

Reference wild type DNA was obtained from Promega (human male genomic DNA). Genomic DNA from human cell line SW480 (containing a homozygous C>A Kras mutation) was purchased from ATCC. Genomic DNA containing a T790M mutation in EGFR exon 20 (H1195 cell line) was also purchased from ATCC. Primers were synthesized by Integrated DNA Technologies.

Primers for PCR reactions

Primers were generated as previously described (see e.g., Li J, Wang L, Mamon H, Kulke M H, Berbeco R, Makrigiorgos G M. Replacing PCR with COLD-PCR enriches variant DNA sequences and redefines the sensitivity of genetic testing. Nat Med 2008; 14:579-84; Milbury C A, Li J, Makrigiorgos G M. ice COLD-PCR enables rapid amplification and robust enrichment for low-abundance unknown DNA mutations. Nucleic Acids Res; 39:e2)

Enrichment Protocols

PCR was performed on the following thermocyclers: ECO thermocycler (Illumina, San Diego, Calif.); For Taqman-based PCR on the Bio-Rad MiniOpticon thermocycler (Bio-Rad Laboratories, Hercules, Calif.); Cepheid thermocycler (Cepheid, Sunnyvale, Calif.)

Sanger Dideoxy-Sequencing

Sequencing was performed as previously described (see e.g., Li J, Wang L, Mamon H, Kulke M H, Berbeco R, Makrigiorgos G M. Replacing PCR with COLD-PCR enriches variant DNA sequences and redefines the sensitivity of genetic testing. Nat Med 2008; 14:579-84; Milbury C A, Li J, Makrigiorgos G M. ice COLD-PCR enables rapid amplification and robust enrichment for low-abundance unknown DNA mutations. Nucleic Acids Res; 39:e2)

Example 1

Limited Denaturation Time (LDT)-COLD-PCR on an ECO Thermocycler

As shown in FIGS. 1 and 2, mutation enrichment was obtained over a number of preferential denautration times Tp (or equivalently: limited denaturation times ($t_L$)) and temperatures on the ECO thermocycler. Applying temperatures above the wild-type Kras amplicon $T_m$ (83.5° C.) for limited times resulted in enrichment of the mutant sequence from about 16% (e.g., 85° C. for 20 seconds) to 83% (e.g., 87° C. for 4 seconds).

As depicted in FIG. 1, higher temperatures (e.g., 87-89° C.) resulted in enrichment of the mutant sequence over a more narrow time window (e.g., 4-8 seconds). Temperatures about 0.5-2.5 degrees above the wild-type $T_m$ (e.g., 84-86° C.) resulted in enrichment of mutant sequences over a broader time window (e.g., 6-20 seconds).

These results indicate that applying a denaturation temperature higher than the wild type $T_m$ for limited time intervals enriched for the amplification of the mutant sequence. As denaturation temperature is increased, the window of time for which the temperature is applied and enrichment occurs is diminished.

Example 2

Limited Denaturation Time (LDT)-COLD-PCR on a Bio-Rad MiniOpticon Thermocycler

As depicted in FIG. 3, limiting the denaturation time ($t_L$) to 10 seconds, as compared to 15 seconds (at 84° C.) increased the discrimination between mutant ("10%") and wild-type ("wt") samples using the Bio-Rad MiniOpticon thermocycler.

These results further confirm that applying a limited denaturation time at or above the Tm of the reference sequence allows for preferential amplification of the mutant amplicon.

Example 3

Limited Denaturation Time (LDT)-COLD-PCR on a Cepheid Thermocycler

As depicted in FIG. 4, mutation enrichment was obtained over a number of limited denaturation times ($t_L$) and temperatures on the Cepheid thermocycler. Applying temperatures at or above the wild-type Kras amplicon $T_m$ (83.5° C.) for limited times resulted in enrichment of the mutant sequence from about 13% (e.g., $T_m$+1 for 2 seconds) to about 55% (e.g., $T_m$ for 1 second).

These results further confirm that as denaturation temperature is increased, the window of time for which the temperature is applied and enrichment occurs is diminished.

I claim:

1. A method for enriching a target sequence, said method comprising:
   (a) subjecting a reaction mixture
      (i) having a reference sequence as part of a reference sequence duplex, and
      (ii) suspected of having a target sequence as part of a target sequence duplex, to a first denaturing temperature that is above the melting temperature (Tm) of the duplexes and for a period of time so as to permit the denaturation of the duplexes, wherein said target sequence is at least 50% homologous to said reference sequence;
   (b) reducing the temperature of the reaction mixture so as to permit formation of target strand/reference strand duplexes having a first melting temperature (first $T_m$) and reference strand/reference strand duplexes having a second melting temperature (second $T_m$), wherein the second $T_m$ is greater than the first $T_m$;
   (c) subjecting the reaction mixture to a denaturing temperature that is equal to or higher than the second $T_m$ for a time, tp, between about 1 second and 90 seconds;
   (d) reducing the temperature of the reaction mixture so as to permit a primer pair to anneal to said target strands;
   (e) extending said primer pair so as to enrich said target sequence relative to said reference sequence, and
   (f) repeating steps (a)-(e) one or more times.

2. The method of claim 1, wherein:
   (i) the target sequence is at least 75%, 80%, 85%, 90%, 95% or more than 95% homologous to said reference sequence;
   (ii) the reference sequence is amplifiable by the primer pair;
   (iii) the reference sequence is not amplifiable by the primer pair;
   (iv) tp is that amount causing at least 10% and not more than 95% denaturation of said target strand/reference strand duplexes;
   (v) tp is that amount causing at least 25% and not more than 75% denaturation of said target strand/reference strand duplexes;

(vi) the temperature of step (c) is a temperature that is less than 5° C. higher than the Tm of said reference sequence, and wherein tp is between about one second and ninety seconds;
(vii) the temperature of step (c) is a temperature that is less than 2° C. higher than the Tm of said reference sequence;
(viii) tp is between one second and twenty seconds;
(ix) steps (a)-(e) are repeated 2-40 times;
(x) the target and reference sequences are first amplified by one or more cycles of PCR prior to step (a);
(xi) the reference sequence is a wild-type allele and the target sequence is a mutant allele;
(xii) the target and reference sequences are 15 to 1000 bases, 25 to 500 bases, or 50 to 200 bases;
(xiii) the method further comprises subjecting said enriched target sequence to further processing;
(xiv) the target sequence or the reference sequence is methylated DNA that has been treated with sodium bisulfite;
(xv) the method further comprises contacting the reaction mixture with reference oligonucleotides; (xvi) the method is used to enrich two or more different target sequences and said method further comprises one or more additional pairs of primers specific to said target sequences; or (xvii) tp is between one second and fifteen seconds.

3. A computer readable medium comprising program instructions for performing the method of claim 1.

4. A system for enriching a target sequence, said system comprising a memory for implementing the program instructions of the computer-readable medium of claim 3.

5. A method comprising:
(a) providing a reaction mixture
  (i) having a reference sequence as part of a reference sequence duplex, and
  (ii) suspected of having a target sequence as part of a target sequence duplex, wherein at least one nucleotide of the target sequence has a different methylation status relative to a corresponding nucleotide on the reference sequence;
(b) subjecting the reaction mixture to a methylation-sensitive treatment to form a mismatch at the at least one nucleotide in the reference sequence duplex or the target sequence duplex;
(c) subjecting the reaction mixture to a first denaturing temperature that is above the melting temperature (Tm) of the duplexes and for a period of time so as to permit the denaturation of the duplexes;
(d) reducing the temperature of the reaction mixture so as to permit formation of target strand/reference strand duplexes having a first melting temperature (first $T_m$) and reference strand/reference strand duplexes having a second melting temperature (second $T_m$);
(e) subjecting the reaction mixture to a denaturing temperature that is equal to or higher than the greater of the first $T_m$, and the second $T_m$, for a time, tp, between about 1 second and 90 ;
(f) reducing the temperature of the reaction mixture so as to permit a primer pair to anneal to said reference strands and target strands; and
(g) extending said primer pair so as to enrich said unmethylated sequences relative to methylated sequences.

6. The method of claim 5, wherein:
(i) the target sequence is at least 75%, 80%, 85%, 90%, 95% or more than 95% homologous to said reference sequence;
(ii) the reference sequence is amplifiable by the primer pair;
(iii) the reference sequence is not amplifiable by the primer pair;
(iv) tp is that amount causing at least 10% and not more than 95% denaturation of said target strand/reference strand duplexes;
(v) tp is that amount causing at least 25% and not more than 75% denaturation of said target strand/reference strand duplexes;
(vi) the temperature of step (e) is a temperature that is less than 5° C. higher than the Tm of said reference sequence, and wherein tp is between about one second and ninety seconds;
(vii) the temperature of step (e) is a temperature that is less than 2° C. higher than the Tm of said reference sequence;
(viii) tp is between one second and twenty seconds;
(ix) steps (a)-(e) are repeated 2-40 times;
(x) the target and reference sequences are first amplified by one or more cycles of PCR prior to step (a);
(xi) the reference sequence is a wild-type allele and the target sequence is a mutant allele;
(xii) the target and reference sequences are 15 to 1000 bases, 25 to 500 bases, or 50 to 200 bases;
(xiii) the method further comprises subjecting said enriched target sequence to further processing;
(xiv) the at least one nucleotide of the target sequence is unmethylated, and the corresponding nucleotide on the reference sequence is methylated; and wherein the second $T_m$, is greater than the first $T_m$;
(xv) the at least one nucleotide of the target sequence is methylated, and the corresponding nucleotide on the reference sequence is unmethylated; and wherein the first $T_m$, is greater than the second $T_m$.
(xvi) the method further comprises contacting the reaction mixture with reference oligonucleotides; (xvii) the method is used to enrich two or more different target sequences and said method further comprises one or more additional pairs of primers specific to said target sequences; or (xviii) tp is between one second and fifteen seconds.

7. A computer readable medium comprising program instructions for performing the method of claim 5.

8. A system for enriching a target sequence, said system comprising a memory for implementing the program instructions of the computer-readable medium of claim 7.

9. The method of claim 5, wherein the methylation-sensitive treatment is treatment with sodium bisulfite.

* * * * *

UNITED STATES PATENT AND TRADEMARK OFFICE
CERTIFICATE OF CORRECTION

PATENT NO. : 10,913,977 B2
APPLICATION NO. : 14/907188
DATED : February 9, 2021
INVENTOR(S) : Gerassimos Makrigiorgos It is certified that error appears in the above-identified patent and that said Letters Patent is hereby corrected as shown below:

In the Claims

In Claim 5, at Column 51, Line 60, the text: "about 1 second and 90 ;" should be replaced with:
-- about 1 second and 90 seconds; --.

In Claim 5, at Column 52, Line 4, the text: "so as to enrich said unmethylated sequences" should be replaced with: -- so as to enrich for unmethylated sequences --.

In Claim 6, at Column 52, Line 44, the text: "and wherein the first $T_m$ is greater than the second $T_m$." should be replaced with: -- and wherein the first $T_m$ is greater than the second $T_m$; --.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*